US009956277B2

(12) United States Patent
Stewart et al.

(10) Patent No.: US 9,956,277 B2
(45) Date of Patent: May 1, 2018

(54) BACILLUS BASED DELIVERY SYSTEM AND METHODS OF USE

(71) Applicant: The Curators of the University of Missouri, Columbia, MO (US)

(72) Inventors: George C. Stewart, Columbia, MO (US); Brian Matthew Thompson, Creve Coeur, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days. days.

(21) Appl. No.: 14/849,123

(22) Filed: Sep. 9, 2015

(65) Prior Publication Data

US 2016/0051656 A1   Feb. 25, 2016

Related U.S. Application Data

(62) Division of application No. 12/391,060, filed on Feb. 23, 2009, now Pat. No. 9,133,251.

(60) Provisional application No. 61/066,801, filed on Feb. 22, 2008.

(51) Int. Cl.
| | |
|---|---|
| *A61K 39/07* | (2006.01) |
| *C12N 15/75* | (2006.01) |
| *C12N 3/00* | (2006.01) |
| *A61K 39/00* | (2006.01) |
| *A61K 39/12* | (2006.01) |
| *C07K 14/32* | (2006.01) |
| *C12N 11/16* | (2006.01) |
| *A61K 35/00* | (2006.01) |

(52) U.S. Cl.
CPC ............ *A61K 39/07* (2013.01); *A61K 39/00* (2013.01); *A61K 39/12* (2013.01); *C07K 14/32* (2013.01); *C12N 3/00* (2013.01); *C12N 11/16* (2013.01); *C12N 15/75* (2013.01); *A61K 2035/11* (2013.01); *A61K 2039/522* (2013.01); *A61K 2039/523* (2013.01); *C07K 2319/035* (2013.01); *C12N 2770/10022* (2013.01); *C12N 2770/10034* (2013.01); *Y02E 50/16* (2013.01); *Y02E 50/17* (2013.01)

(58) Field of Classification Search
CPC .. C07K 14/32; C07K 2319/035; C12N 11/16; C12N 15/75; C12N 2770/10022; C12N 2770/10; A61K 2035/11; A61K 2039/522; A61K 2039/523; A61K 39/00; A61K 39/07; A61K 39/12
USPC ....... 435/170, 252.31, 262.5, 485; 424/190.1
See application file for complete search history.

(56) References Cited

U.S. PATENT DOCUMENTS 8,030,064 B2   10/2011 Lee et al.

FOREIGN PATENT DOCUMENTS

| EP | 0 792 363 B1 | 12/2003 |
|---|---|---|
| WO | 02/00232 A2 | 1/2002 |
| WO | 2005/028654 A1 | 3/2005 |
| WO | 2006/012366 A2 | 2/2006 |
| WO | 2007/078127 A1 | 7/2007 |
| WO | 2007/086898 A2 | 8/2007 |

OTHER PUBLICATIONS

Thompson, Amino-Terminal Sequences of the Bacillus Anthracis Exosporium Proteins BCLA and BCLB Important for Localization and Attachment to the Spore Surface, MS Thesis, Aug. 2008, pp. 1-165.*
Ciabattini, A., et al., "Oral Priming of Mice by Recombinant Spores of Bacillus subtilis," Vaccine, Oct. 2004, pp. 4139-4143, vol. 22, Nos. 31-32.
Duc, L. H., et al., "Immunization Against Anthrax Using Bacillus subtilis Spores expressing the Anthrax Protective Antigen," Vaccine, Jan. 2007, pp. 346-355, vol. 25, No. 2.
Duc, L. H., et al., "Bacterial Spores as Vaccine Vehicles," Infection and Immunity, May 2003, pp. 2810-2818, vol. 71, No. 5.
Isticato, R., et al., "Surface Display of Recombinant Proteins in Bacillus subtilis Spores," Journal of Bacteriology, Nov. 2001, pp. 6294-6301, vol. 183, No. 21.
Johnson, M. J., et al., "ExsY and CotY are Required for the Correct Assembly of the Exosporium and Spore Coat of Bacillus cereus," Journal of Bacteriology, Nov. 2006, pp. 7905-7913, vol. 188, No. 22.
Kim, J. H., et al., "Spore-Displayed Streptavidin: A Live Diagnostic Tool in Biotechnology," Biochemical and Biophysical Research Communications, May 2005, pp. 210-214, vol. 331, No. 1.
Kim, J. H., et al., "Bacterial Surface Display of GFP(uv) on Bacillus subtilis Spores," Journal of Microbiology and Biotechnology, Apr. 2007, pp. 677-680, vol. 17, No. 4.
Luiz, W. B., et al., "Boosting Systemic and Secreted Antibody Responses in Mice Orally Immunized with Recombinant Bacillus subtilis Strains Following Parenteral Priming with a DNA Vaccine Encoding the Enterotoxigenic *Escherichia coli* (ETEC) CFA/I fimbriae B subunit," Vaccine, 2008, pp. 3998-4005, vol. 26, No. 32.
Mauriello, E. M., et al., "Display of Heterologous Antigens on the Bacillus subtilis Spore Coat Using CotC as a Fusion Partner," Vaccine, Mar. 2004, pp. 1177-1187, vol. 22, Nos. 9-10.
Paccez, J. D., et al., "Stable Episomal Expression System Under Control of A Stress Inducible Promoter Enhances the Immunogenicity of Bacillus subtilis as a Vector for Antigen Delivery," Vaccine, Apr. 2006, pp. 2935-2943, vol. 24, No. 15.
Paccez, J. D., et al., "Evaluation of Different Promoter Sequences and Antigen Sorting Signals on the Immunogenicity of Bacillus subtilis Vaccine Vehicles," Vaccine, Jun. 2007, pp. 4671-4680, vol. 25, No. 24.

(Continued)

*Primary Examiner* — Janet L Epps-Smith
(74) *Attorney, Agent, or Firm* — Senniger Powers LLP

(57) ABSTRACT

Herein a *Bacillus* exosporium antigen delivery (BEAD) system that provides a means to introduce recombinant proteins or small molecules into the exosporium of members of the *B. cereus* family of bacteria, i.e. *B. anthracis, B. cereus,* and *B. thuringiensis*, is disclosed. The system results in the surface display of recombinant proteins or small molecules such that they can stimulate an immune response. In addition, methods of making and using the system are described.

23 Claims, 20 Drawing Sheets
(18 of 20 Drawing Sheet(s) Filed in Color)

(56) References Cited

OTHER PUBLICATIONS

Park, T. J., "Surface-Display of Recombinant Proteins on Bacterial Exosporium and its Biotechnological Applications," Doctoral Thesis presented to the Department of Chemical and Biomolecular Engineering, Korea Advanced Institute of Science and Technology, 2004, 104 pages.
Sequence Listing filed in WO 2007/078127 A1 published Jul. 12, 2007, downloaded from <http://patentscope.wipo.int/search/en/detail.jsf?docId=WO2007078127&recNum=1&tab=PCTDocuments&maxRec=&office=&prevFilter=&sortOption=&queryString=>, 5 pages.
Steichen, C. T., et al., "Non-Uniform Assembly of the Bacillus anthracis Exosporium and a Bottle Cap Model for Spore Germination and Outgrowth," Molecular Microbiology, 2007, pp. 359-367, vol. 64, No. 2.
Thompson, B. M., et al., "The BclB Glycoprotein of Bacillus anthracis Is Involved in Exosporium Integrity," Journal of Bacteriology, Sep. 2007, pp. 6704-6713, vol. 189, No. 18.
Waller, L. N., et al., "Identification of a Second Collagen-Like Glycoprotein Produced by Bacillus anthracis and Demonstration of Associated Spore-Specific Sugars," Journal of Bacteriology, Jul. 2005, pp. 4592-4597, vol. 187, No. 13.
Zhou, Z., et al., "Oral Administration of a Bacillus subtilis Spore-Based Vaccine Expressing Clonorchis sinensis tegumental Protein 22.3 kDa Confers Protection Against Clonorchis sinensis," Vaccine, Mar. 2008, pp. 1817-1825, vol. 26, No. 15.
Zhou, Z., et al., "Immunogenicity of Recombinant Bacillus subtilis Spores Expressing Clonorchis sinensis tegumental Protein," Parasitology Research, Jan. 2008, pp. 293-297, vol. 102, No. 2.

\* cited by examiner

FIG. 1

B. anthracis spore

Exosporium nap (BclA)
Exosporium basal layer
Spore coat
Cortex

FIG. 2A

| | |
|---|---|
| MSNNNYSNGLNPDESLSASAFDPNLVGPTLPPIPPFTLPTG | SEQ. ID. NO: 7 |
| MSEKYIILHGTALEPNLIGPTLPPIPPFTFPNG | SEQ. ID. NO: 8 |
| MVKVVEGNGGKSKIKSPLNSNFKILSDLVGPTFPPVFTGMTGIT | SEQ. ID. NO: 9 |
| MKQNDKLWLDKGIIGPENIGPTFPVLPPIHIPTG | SEQ. ID. NO: 10 |
| LI/VGPTL/FPPIPP | SEQ. ID. NO: 11 |

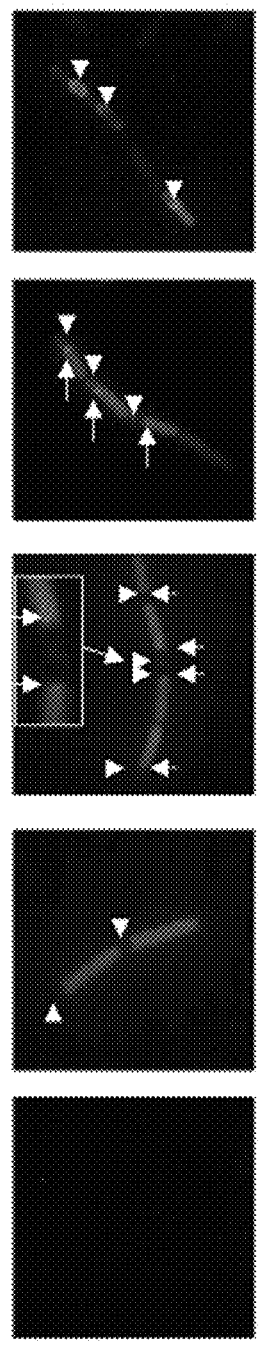
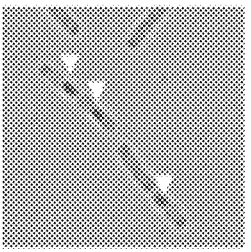
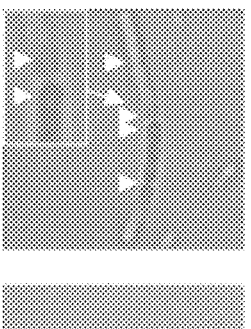
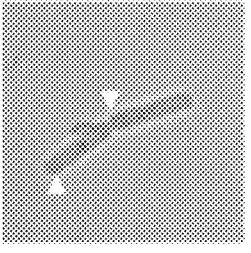
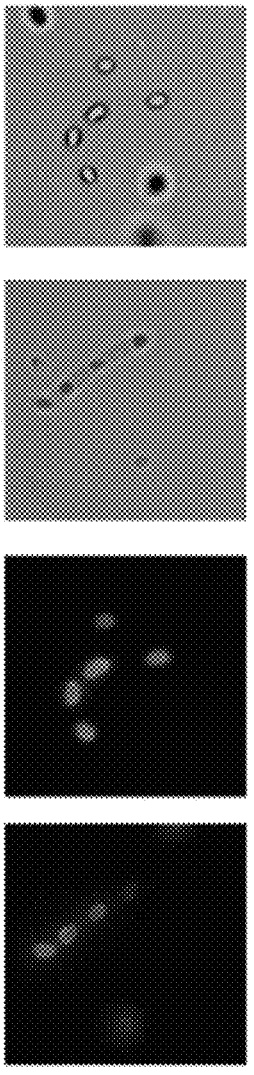

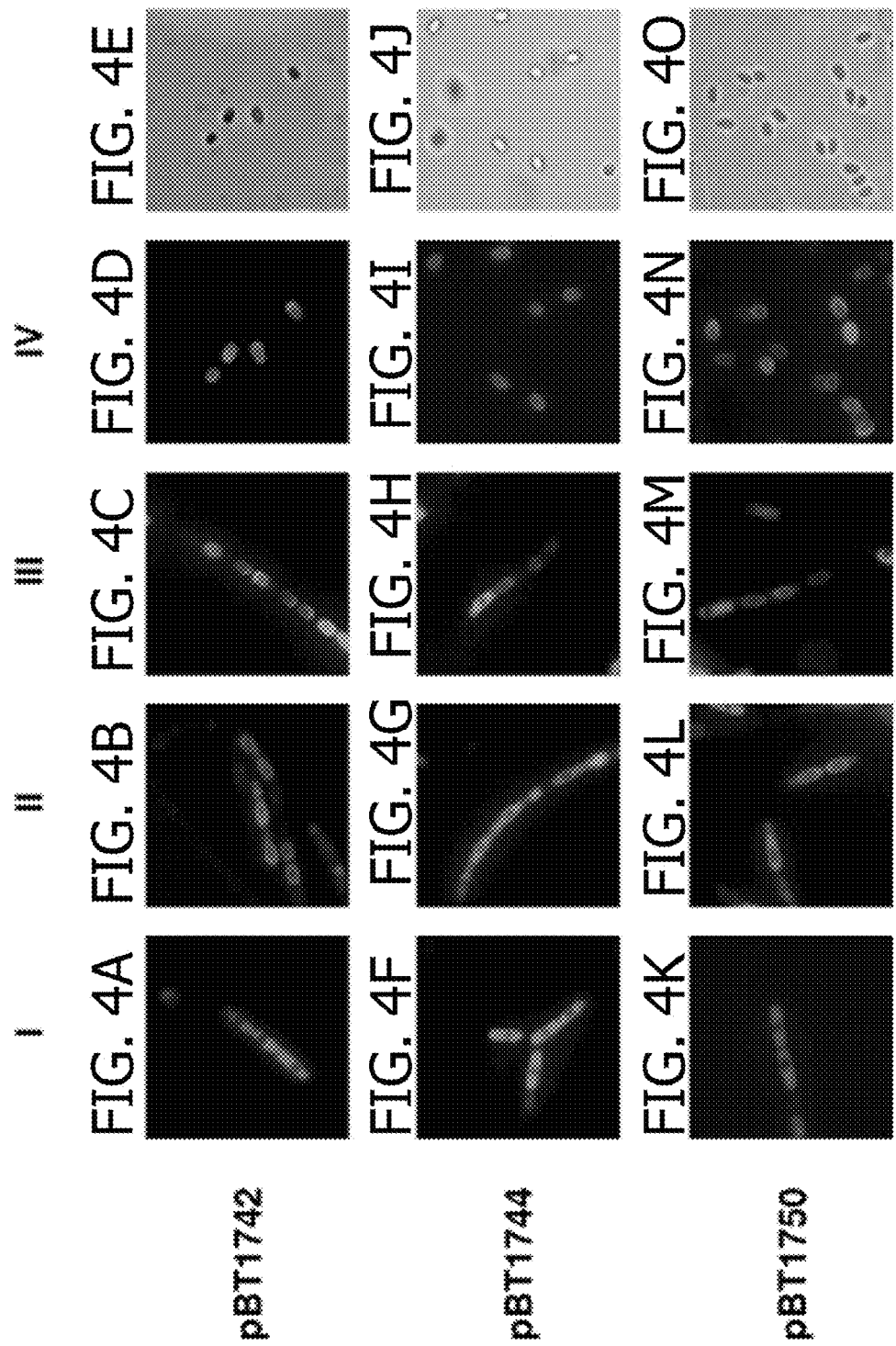

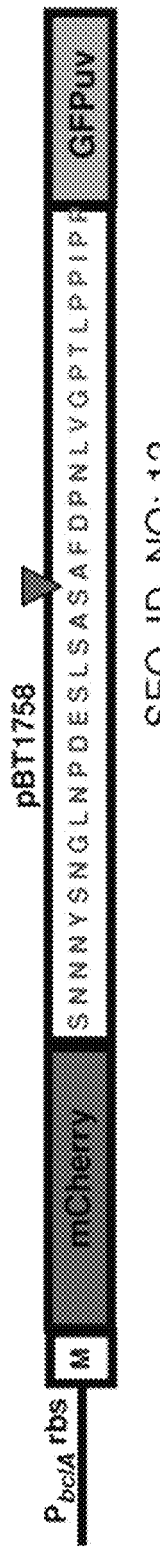
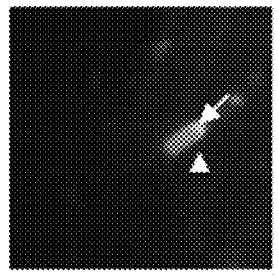
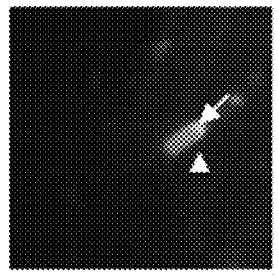
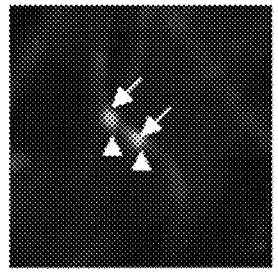
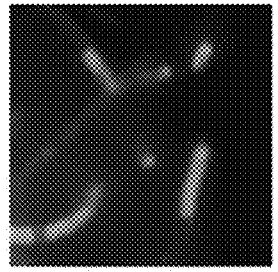
FIG. 5A
FIG. 5B
FIG. 5C
FIG. 5D
FIG. 5E

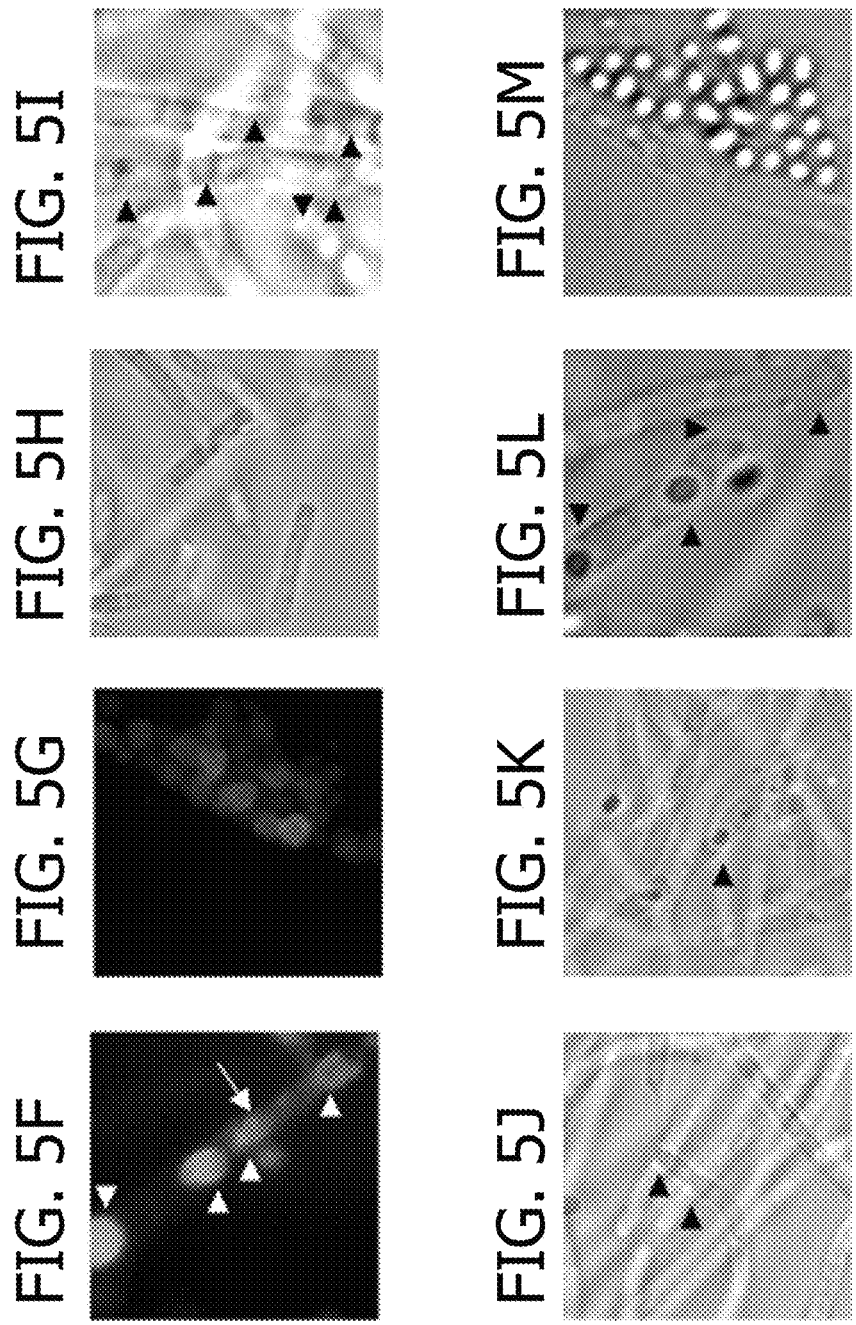

FIG. 6A FIG. 6B FIG. 6C FIG. 6D FIG. 6E
FIG. 6F FIG. 6G FIG. 6H FIG. 6I FIG. 6J
FIG. 6K FIG. 6L FIG. 6M FIG. 6N FIG. 6O pBT1693
pBT1694
pBT1729

I  II  III  IV

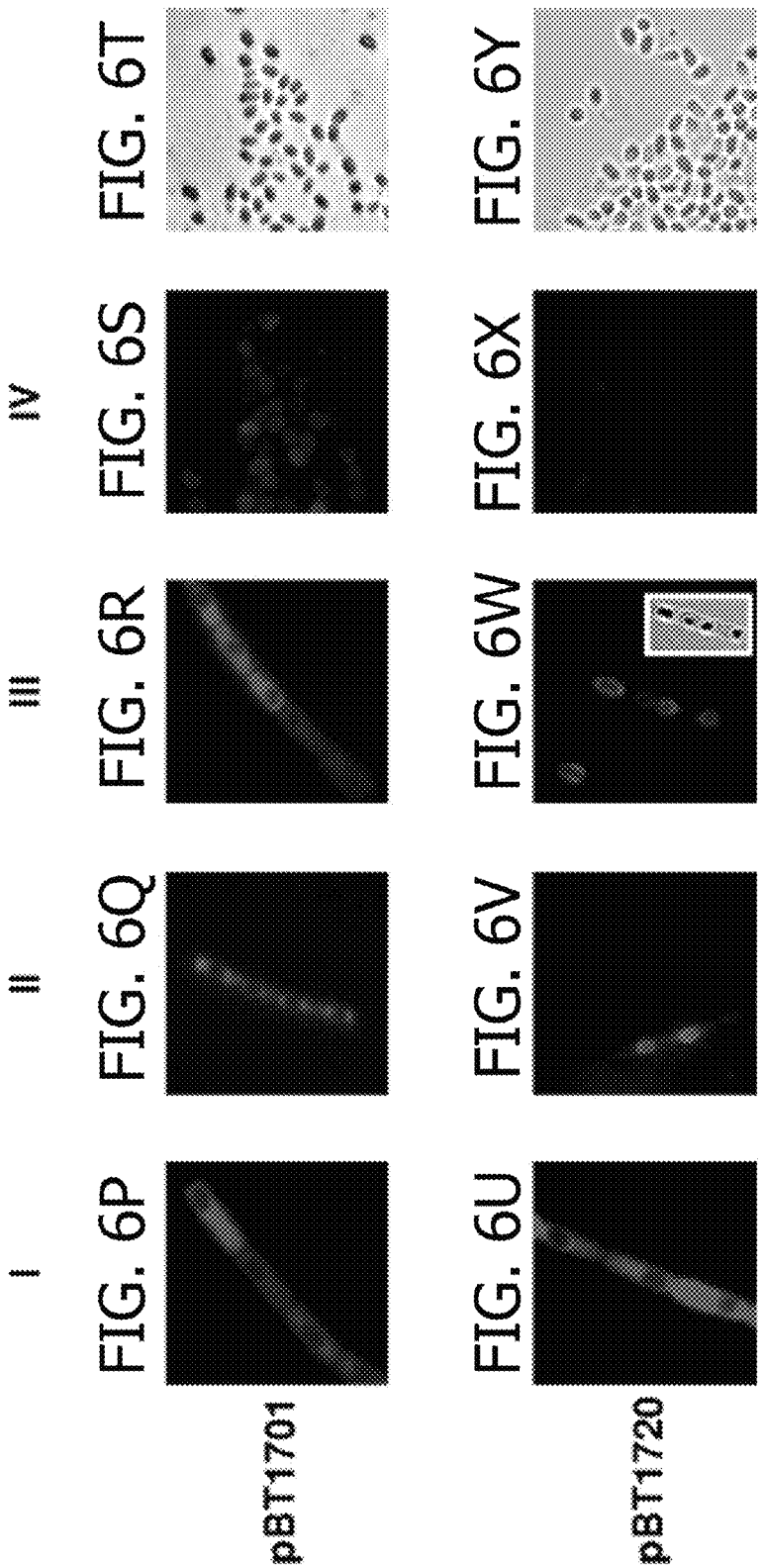

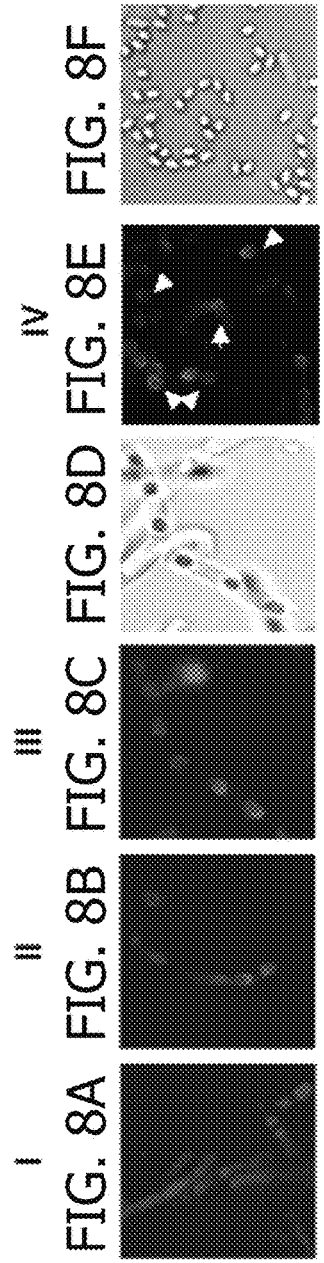
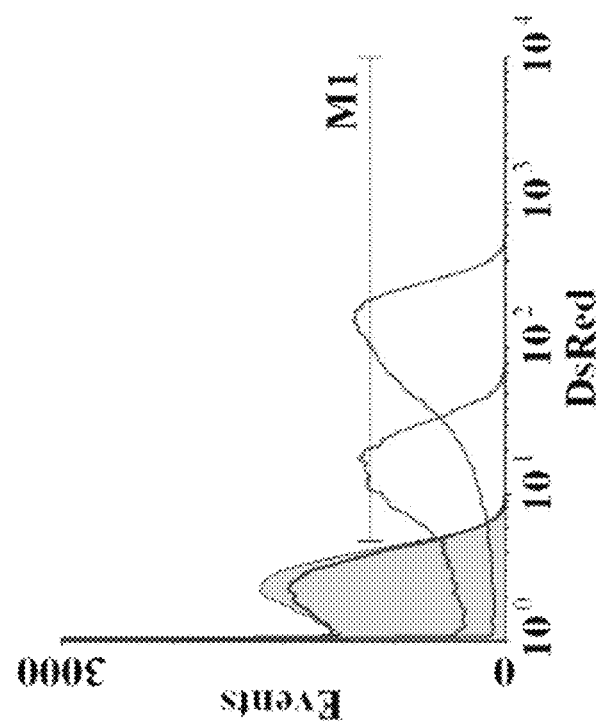

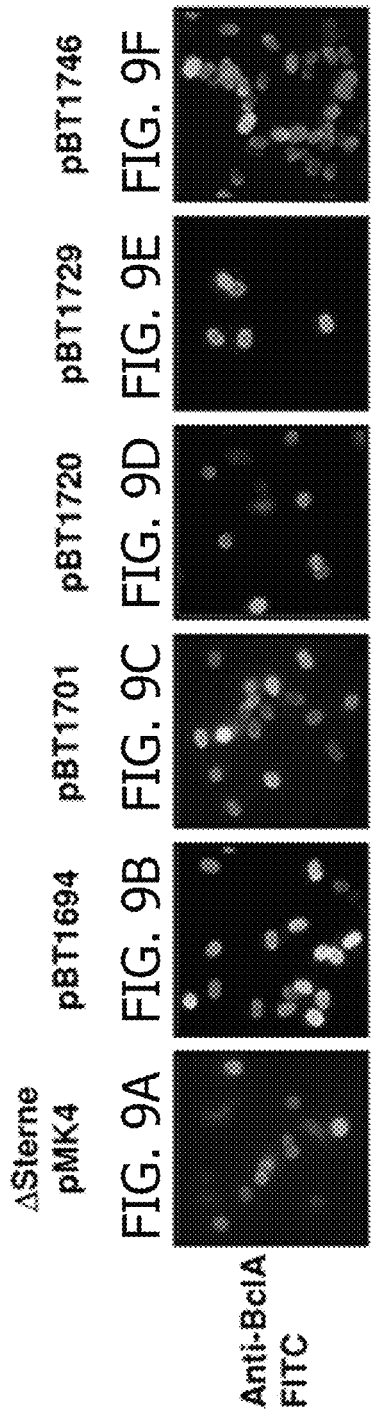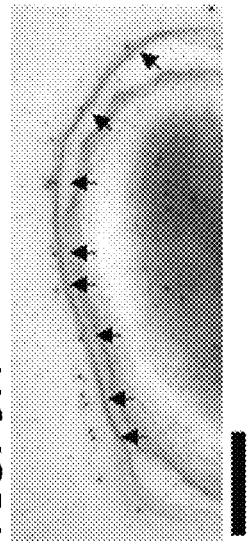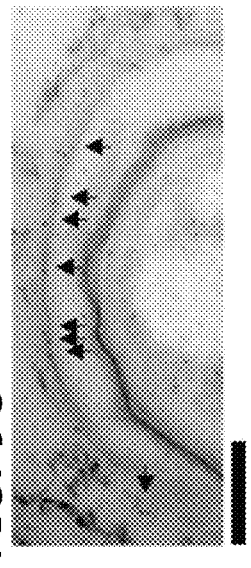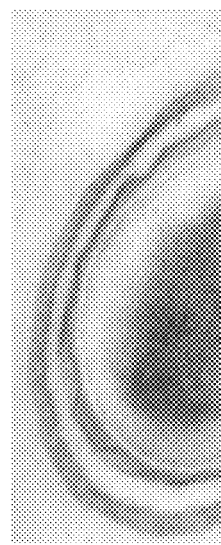

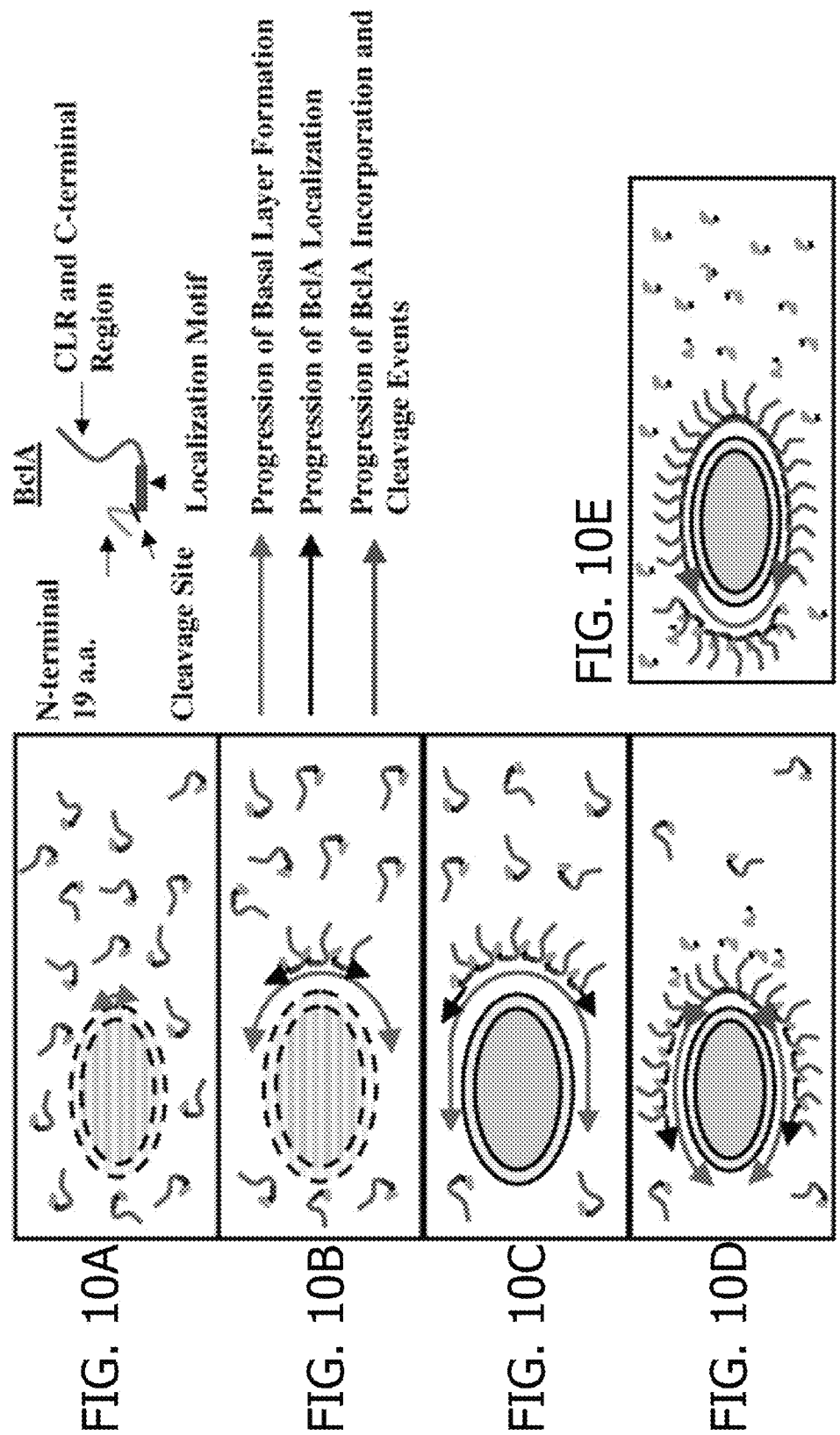

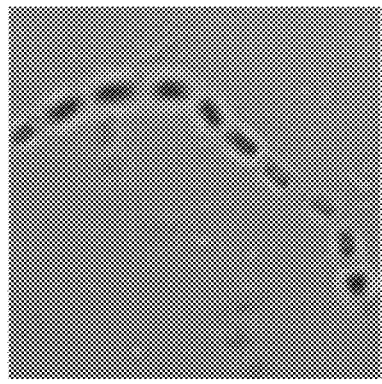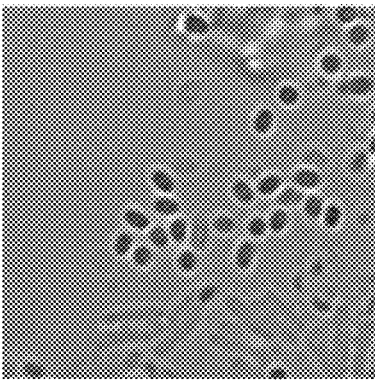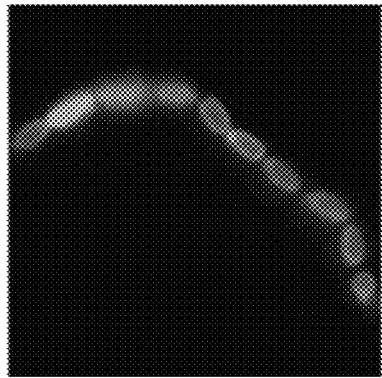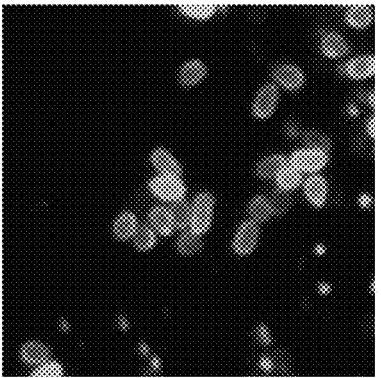

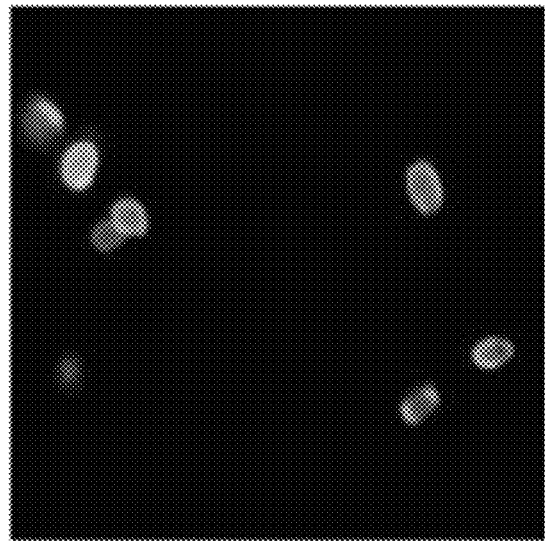
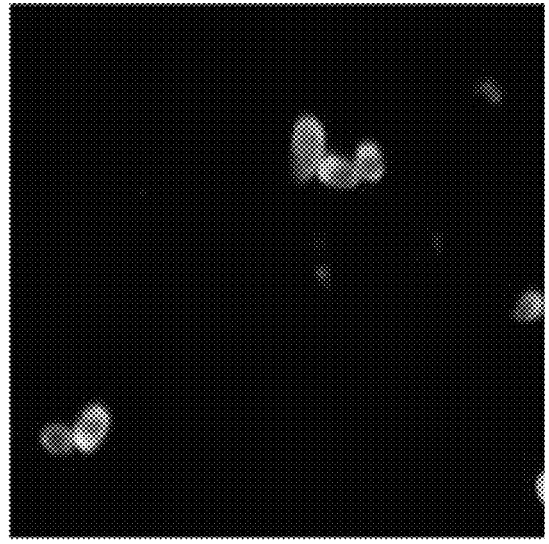
FIG. 12B
FIG. 12A

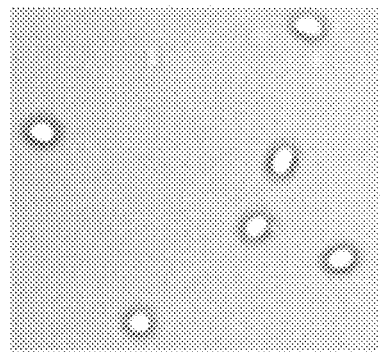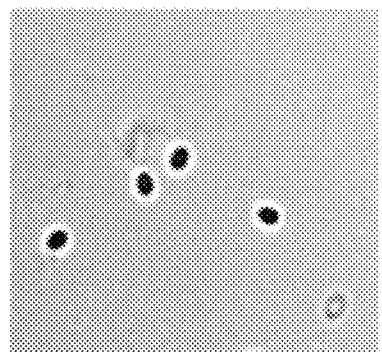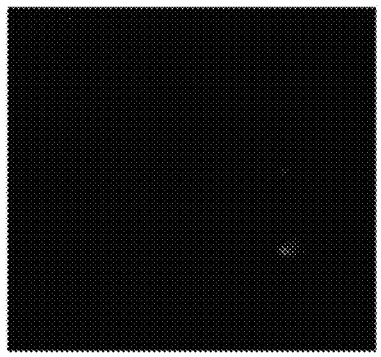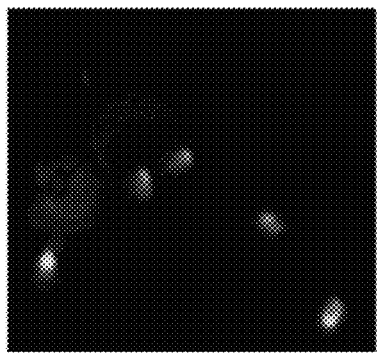

FIG. 15

BACILLUS BASED DELIVERY SYSTEM AND METHODS OF USE

RELATED APPLICATIONS

This application is a divisional of U.S. patent application Ser. No. 12/391,060, filed on Feb. 23, 2009, which claims priority to U.S. Provisional Patent Application No. 61/066,801, which was filed Feb. 22, 2008. Each of the above-cited applications is incorporated herein by reference in its entirety.

All applications are commonly owned.

FIELD OF THE INVENTION

The present invention relates to a system suitable for the delivery of diagnostic, immunogenic, or therapeutic compositions to a host cell either in vivo or in vitro. The invention provides both compositions and methods of use relating to the system. The system utilizes sequences from *Bacillus* spp. glycoproteins to insert antigenic material or reporter proteins into the exosporium of a *Bacillus* spore and carry the antigenic material or reporter protein to a target site as part of a delivery system.

BACKGROUND OF THE INVENTION

*Bacillus* is a genus of rod-shaped bacteria. Ubiquitous in nature, *Bacillus* includes both free-living and pathogenic species. There are three important pathogenic members of *Bacillus*: *B. cereus* causes a foodborne illness similar to that of *Staphylococcus*; *B. thuringiensis* is an important insect pathogen, and is sometimes used to control insect pests; and *B. anthracis* causes anthrax in humans and animals. In humans, three types of anthrax occur: cutaneous, gastrointestinal, and pulmonary anthrax. Under stressful environmental conditions, these cells shift to an alternative developmental pathway, sporulation, and produce oval endospores that can stay dormant for extended periods. *Bacillus anthracis* is infectious in the endospore form.

Much of what is known of the sporulation process comes from genetic studies of the nonpathogenic *Bacillus subtilis*. Unlike the pathogenic *Bacillus* spp. above, *B. subtilis* does not have an exosporium layer on its exterior. This outermost layer of the endospore consists of a basal layer surrounded by an external nap of hair-like projections (see FIG. 1). Filaments of the hair-like nap are predominantly formed by the collagen-like glycoprotein BclA, while the basal layer is comprised of a number of different proteins.

Relatively little is known about the exosporium layer because of the difficulty in genetically manipulating the exosporium-containing species. Several proteins have been identified as being associated with the exosporium, or their loss is associated with defects in exosporium assembly. The components of the outer spore layers are thought to be produced in the mother cell and then assembled on the developing spore. Many of these components are expressed during the sporulation cycle by RNA polymerase bearing the $\sigma^K$ factor. Although the exosporium layer does not appear to be essential for virulence and does not confer the principal resistance properties to the spore, its location on the spore suggests that it plays a role in initial host-spore interactions. It is also an important source of spore antigens which may enhance the protective effect of current vaccines.

While spores of *B. subtilis* have been proposed as vaccine delivery vehicles using CotB and CotC fusion proteins, such a system is unlikely to function with the *B. cereus* family of bacteria, i.e. *B. anthracis*, *B. cereus*, and *B. thuringiensis*. These bacteria include the exosporium layer that is likely to prevent fusions to CotB or CotC from being exposed on the surface and available as delivery vehicles. Because anthrax, especially pulmonary anthrax, is an acute, fatal disease and may potentially be utilized as a bioterrorism weapon, a system to delivery immunogenic antigens or other therapeutic molecules effective against anthrax is desired. Herein, such a system is described.

SUMMARY OF THE INVENTION

The invention provides a *Bacillus* exosporium antigen delivery (BEAD) system suitable for delivering therapeutic, immunogenic, or diagnostic compositions to a subject. The system comprises a recombinant *Bacillus cereus* family member includes a fusion construct on the exterior of its exosporium. Fusion constructs comprise an immunogenic molecule and at least the first 24 amino acid residues of the N-terminal domain (NTD) of a *Bacillus* exosporium protein. A fusion construct is inserted into the exosporium such that the immunogenic molecule portion of the fusion construct is physically oriented to be able to stimulate an immune response.

A BEAD system of the invention may include a recombinant *Bacillus cereus* family member that has multiple fusion constructs on its exosporium. In such systems, one or more immunogenic molecules may be included such that a multivalent therapeutic effect may be achieved in a subject to whom the BEAD system is administered. Alternatively, a BEAD system may include multiple recombinant *Bacillus cereus* family members, each of which includes a single type of fusion construct on its respective exosporium. A combination of such multiple *Bacillus cereus* family members may be used in a BEAD system to achieve a multivalent therapeutic effect in a subject to whom the BEAD system is delivered.

Recombinant *Bacillus cereus* family members include strains of *B. anthracis*, *B. cereus*, *B. thuringiensis*, and combinations thereof. Strains of *B. anthracis* are preferred members. Inactivated strains are also preferred. Alternatively, nontoxic or genetically manipulated *Bacillus cereus* family members may be used. Preferably, recombinant *B. cereus* family member cultures are prepared separately then combined together after harvest. Alternatively, *B. cereus* family members may be prepared in combination with one another from the beginning.

Fusion constructs preferably include at least the first 35 amino acid residues of the N-terminal domain (NTD) of a *Bacillus* exosporium protein. Fusion constructs may even include complete *Bacillus* exosporium proteins. Preferred *Bacillus* exosporium proteins include *Bacillus* BclA, BclB, BAS3290 (BclE), and combinations thereof.

The invention also provides methods of making a BEAD system comprising constructing a fusion construct; cloning the fusion construct into a shuttle plasmid; and electroporating the shuttle plasmid containing the fusion construct into a *Bacillus cereus* family member such that the fusion construct is expressed on the family member's exosporium.

The invention further provides kits for a BEAD system comprising a recombinant *Bacillus cereus* family member expressing a fusion construct comprising an immunogenic molecule and at least the first 24 amino acid residues of the N-terminal domain (NTD) of a *Bacillus* exosporium protein, wherein the recombinant *Bacillus cereus* family member's exosporium expresses the fusion construct such that the immunogenic molecule is physically oriented to be able to stimulate an immune response. Preferred kits include an immunogenic molecule and at least the first 35 amino acid residues of the N-terminal domain (NTD) of a *Bacillus* exosporium protein.

Method of using a BEAD system are also provided. Such methods comprise administering to a subject a recombinant *Bacillus cereus* family member expressing a fusion construct, wherein the fusion construct comprises an immunogenic molecule and at least the first 24 amino acid residues of the N-terminal domain (NTD) of a *Bacillus* exosporium protein, in the recombinant *Bacillus cereus* family member's exosporium such that the immunogenic molecule of the fusion construct is physically oriented to be able to stimulate an immune response.

An "immunogenic molecule" means a recombinant protein, native protein, or artificial small molecule that stimulates an immune response in a subject. Preferably, an immunogenic molecule does not adversely effect a subject when administered.

Herein, a "subject" may be a human or animal. "Animal" refers to a fish, bird, or mammal. Preferably the animal is a mammal such as a cat, dog, ungulate (e.g. horse, zebra, donkey, cattle/bison, rhinoceros, camel, hippopotamus, goat, swine, sheep, giraffe, okapi, moose, deer, tapir, antelope, or gazelle), rodent (e.g. mice, rats, and other small, gnawing mammals), bat, bear, primate, or cetacean.

An "immune response" or "immunological response" means, but is not limited to, the development of a cellular and/or antibody-mediated immune response to the composition or vaccine of interest. Usually, an immune or immunological response includes, but is not limited to, one or more of the following effects: the production or activation of antibodies, B cells, helper T cells, suppressor T cells, and/or cytotoxic T cells, directed specifically to an antigen or antigens included in the composition or vaccine of interest. Preferably, the subject will display either a therapeutic or a protective immunological (memory) response such that resistance to new infection will be enhanced and/or the clinical severity of the disease reduced. Such protection will be demonstrated by either a reduction in number of symptoms, severity of symptoms, or the lack of one or more of the symptoms associated with the infection of a pathogen, and/or a delay in the of onset of symptoms.

Those of skill in the art will understand that the compositions disclosed herein may incorporate known injectable, physiologically acceptable sterile solutions. For preparing a ready-to-use solution for parenteral injection or infusion, aqueous isotonic solutions, e.g. saline or plasma protein solutions, are readily available. In addition, the compositions of the present invention can include diluents, isotonic agents, stabilizers, or adjuvants.

"Diluents", as used herein, can include water, saline, dextrose, ethanol, glycerol, and the like. "Isotonic agents" can include sodium chloride, dextrose, mannitol, sorbitol, and lactose, among others. "Stabilizers" include albumin and alkali salts of ethylendiamintetracetic acid, among others.

Herein, an "adjuvant" or "adjuvants" can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), non-metabolizable oil, mineral and/or plant/vegetable and/or animal oils, polymers, carbomers, surfactants, natural organic compounds, plant extracts, carbohydrates, water-in-oil emulsion, oil-in-water emulsion, and water-in-oil-in-water emulsion. The emulsion can be based in particular on light liquid paraffin oil (European Pharmacopeia type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di(caprylate/caprate), glyceryl tri-(caprylate/caprate) or propylene glycol dioleate; or esters of branched fatty acids or alcohols, in particular isostearic acid esters. The oil is used in combination with emulsifiers to form the emulsion. The emulsifiers are preferably nonionic surfactants, in particular esters of sorbitan, mannide (e.g. anhydromannitol oleate), glycol, polyglycerol, propylene glycol, and oleic, isostearic, ricinoleic or hydroxystearic acid, which are optionally ethoxylated, and polyoxypropylene-polyoxyethylene copolymer blocks, in particular the Pluronic products, especially L121. (See Hunter et al., The Theory and Practical Application of Adjuvants (Ed. Stewart-Tull, D. E. S.), John Wiley and Sons, NY, pp 51-94 (1995) and Todd et al., Vaccine 15:564-570 (1997).

Compositions of the invention also can include one or more pharmaceutical-acceptable earners. Herein, "pharmaceutical-acceptable carrier" or "veterinary-acceptable carrier" include any and all solvents, dispersion media, coatings, stabilizing agents, growth media, dispersion media, cell culture media and cell culture constituents, coatings, adjuvants, diluents, preservatives, antibacterial and antifungal agents, isotonic agents, adsorption delaying agents, and the like.

"Administering" or the "administration of" a composition of the invention means delivery of a composition of the invention to a subject by any accepted means in the art. Such appropriate means of administration include intravenous, intraarterial, intraperitoneal, intramuscular, subcutaneous, intrapleural, topical, or by inhalation. The appropriate means of administering a composition of the invention to a subject will be dependent upon the specific objective to be achieved (e.g. therapeutic, diagnostic, preventative) and the targeted cells, tissues, or organs.

Herein, "effective dose" means, but is not limited to, an amount of a composition of the invention that elicits, or is able to elicit, an immune response that yields a reduction of clinical symptoms in a subject to which the antigen is administered.

"Isolated" means altered "by the hand of man" from its natural state, i.e., if it occurs in nature, it has been changed or removed from its original environment, or both. For example, a polynucleotide or polypeptide naturally present in a living organism is not "isolated," but the same polynucleotide or polypeptide separated from the coexisting materials of its natural state is "isolated", as the term is employed herein.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein. The application contains at least one drawing executed in color. Copies of this patent application publication with color drawing(s) will be provided by the Office upon request and payment of the necessary fee.

FIG. 1 shows a transmission electron micrograph of a spore of the Sterne strain of *B. anthracis*. The sample was stained with ruthenium red to better visualize the nap on the exosporium layer. The cortex, spore coat, exosporium nap (BclA), and exosporium basal layer of the spore are indicated.

FIG. 2A is a N-terminal sequence alignment of four *B. anthracis* collagen-like proteins. Each protein sequence is displayed beginning with the N-terminal methionine residue. The conserved region is underlined in each sequence. A consensus sequence (SEQ ID NO: 11) is presented below the alignment. GenBank designations of the Sterne strain are as follows: SEQ ID NO: 7 is BclA; SEQ ID NO: 8 is BAS3290 (BclE); SEQ ID NO: 9 is BAS4623; and SEQ ID NO: 10 is BclB.

FIGS. 3A-O provide micrographs (epi-fluorescence microscopy at 600× magnification) of sporulating cells expressing the pBT1744 BclA N-terminal domain fusion and tracks expression over time. Arrowheads correspond to spores at various stages of development; arrows indicate BclA fusion localization to the spore poles. FIGS. 3F-3J, 3M, and 3N are bright field images of the epi-fluorescence images FIGS. 3A-3E, 3K and 3L, respectively. Insets in FIGS. 3C and 3H are enlarged images of the filament to enable visualization of the initial polar fusion protein localization and the site of spore development respectively. FIGS. 3A-3N specifically show the following stages. FIGS. 3A and 3F: $T_{-1.5}$, cells taken at mid-exponential phase. FIGS. 3B and 3G: $T_2$, appearance of fluorescence in the mother cell cytoplasm and the appearance of the darkened area representative of spore development (enlarged 150% for better visualization). FIGS. 3C and 3H: $T_3$, beginning of localization of BclA to the site of initiation of exosporium assembly, as noted by the small enhancement of the fluorescence at the internal pole of the developing spores. FIGS. 3D and 3I: $T_4$, progression of BclA localization of BclA around the pole of the spore at a time corresponding with the appearance of visible spores by bright field microscopy. FIGS. 3E and 3J: $T_6$, localization of BclA around the spore progressing towards completion. FIGS. 3K and 3M: $T_7$, progression of BclA localization near completion. FIGS. 3L and 3N: $T_{10}$, free fluorescent spores with the pBT1744-encoded fusions attached to the exosporium. FIG. 3O graphs the progression of the sporulating culture over time as monitored by absorbance at 600 nm. Initiation of stationary phase equals $T_0$. Cells were induced to sporulate synchronously in modified G broth. Samples were taken at the indicated times.

FIGS. 4A-4O show micrographs of sporulating cells and spores from strains expressing the entire BclA open reading frame (ORF) (pBT1742), the N-terminal domain (pBT1744), and the N-terminal truncation (pBT1750) fusion constructs (600× magnification). Roman numerals at the top of the figure correspond to spore developmental stages of cells bearing the BclA N-terminal domain fusions: I, appearance of the fusion protein in the mother cell cytoplasm; II, concentration of the protein around the spore periphery (18-22 h); III, loss of fluorescence from the mother cell cytoplasm (22-24 h); and IV, released spores (>24 h). FIGS. 4E, 4J, and 4O are bright field images of the free spores whose fluorescence is shown in FIGS. 4D, 4I, and 4N, respectively.

FIG. 5A diagrams the pBT1758-encoded fusion construct. The reported cleavage site is denoted by a triangle (▼). FIGS. 5B-5M show micrographs of the pBT1758 fusion in stages corresponding to time points outlined in FIGS. 4A-4O. Arrowheads denote developing spore locations; arrows denote locations of cleavage of the N-terminal sequence of BclA. FIGS. 5B and 5H show early sporulation, production of the pBT1758 fusion throughout mother cell cytoplasm. FIGS. 5C and 5I show progression of the pBT1758 fusion around the pole of the spore. The transition from dark orange to light orange corresponds with the initiation of the cleavage of the GFPuv and mCherry reporters. FIGS. 5D and 5J show that as the pBT1758-encoded fusion localizes across the midpoint of the spore, the cleavage event initiates and follows the localization across the spore, resulting in the yellow colour of the separating GFPuv and mCherry reporters (arrows). FIGS. 5E and 5K show that complete localization of the pBT1758 fusion has occurred, with the cleavage event (yellow) almost completed its migration around the spore towards the distal pole of the sporulating cell (arrow). The GFPuv reporter is incorporated into the newly visible spore at this point, and the mCherry reporter is free in the mother cell cytoplasm. FIGS. 5F and 5L demonstrate three progressive time points occurring in a common filament. The cells at the top are devoid of mCherry, via leakage of the mother cell cytoplasmic contents or degradation of the mCherry reporter. FIGS. 5G and 5M show released spores are coated with the cleaved pBT1758-encoded product (GFPuv). Magnifications of FIGS. 5B, 5D, 5E, 5H, 5J and 5K were at 600×, and of FIGS. 5C, 5F, 5G, 5I, 5L and 5M were at 1000×.

FIGS. 6A-6D, 6F-6I, 6K-6N, 6P-6S, and 6U-6X shows micrographs of sporulating cells and spores (600× magnification) from strains expressing the BclA N-terminal domain GFPuv (pBT1693), BclA N-terminal domain DsRed (pBT1694), DsRed control (pBT1729), the deleted motif (pBT1701) and the conserved motif-only (pBT1720) fusion constructs. Stages indicated above the micrographs correspond to those described in FIGS. 4A-4O. FIGS. 6E, 6J, 6O, 6T and 6Y are bright field images of FIGS. 6D, 6I, 6N, 6S and 6X respectively.

FIGS. 8A-8F show micrographs of sporulating cells and spores (600×) from strains expressing the pBT1746-encoded fusion (containing the bclA promoter and BclB N-terminal domain) at the developmental stages I-IV described in FIGS. 4A-4O. Arrowheads denote poles of free spores devoid of fluorescence. FIGS. 8D and 8F are bright field images of the spores or sporulating cells whose fluorescence is shown in FIGS. 8C and 8E respectively. FIG. 8G shows a flow cytometry histogram of spores containing fusion constructs from pBT1746 (purple, i.e. middle curve), pBT1747 (bclB promoter and BclB N-terminal domain; blue, i.e. far left curve within grey area), pBT1694 (BclA N-terminal domain-DsRed; red, i.e. far right curve) and control pMK4 in ΔSterne (grey area).

FIGS. 9A-9F are micrographs of spores obtained from cells containing DsRed fusion constructs after immunolabeling with polyclonal rabbit anti-rBclA antibodies and FITC-protein A. Native BclA stained areas appear green, fusion proteins appear red, and co-localization results in a yellow color. pBT1694, BclA N-terminal domain fused to DsRed; pBT1701, BclA N-terminal domain deleted for the conserved domain sequence fused to DsRed; pBT1720, BclA conserved motif only fused to DsRed; pBT1729, DsRed lacking BclA residues; and pBT1746, DsRed bearing the BclB N-terminal domain expressed under the direction of the bclA promoter. FIGS. 9G-9I are TEM micrographs of spores containing the BclA NTD fusion to eGFP (pBT1744). FIG. 9G shows pBT1744 fusion spores labelled with rabbit polyclonal anti-GFP antibodies followed by anti-rabbit secondary labelled with 10 nm colloidal gold particles. FIG. 9H shows pBT1744 fusion spores labelled with rabbit anti-rBclA polyclonal antibodies followed by secondary anti-rabbit antibodies labelled with 20 nm colloidal gold particles. FIG. 9I shows ΔSterne control spores labelled with pre-immune rabbit polyclonal antibodies and 20 nm colloidal gold particles. Examples of gold particles are denoted by arrows. The bar represents a 250 nm size and applies to FIGS. 9G-9I.

FIGS. 10A-10E show a model for BclA incorporation into the exosporium basal layer during sporulation in *B. anthracis*. FIG. 10A shows production of BclA and appearance of fluorescence in the mother cell cytoplasm. FIG. 10B represents the localization of BclA to the pole of the spore (facing the mother cell compartment) following the progression (light purple or gray double headed arrow) of the basal layer (dashed lines) around the spore. FIG. 10C shows the appearance of a visible spore (solid lines), and continuation of BclA localization (black arrows) around the spore. FIG. 10D illustrates the progression of BclA localization across the spore (light purple or gray long arrows), with a tailing cleavage event (darker gray or purple short arrows) that incorporates the localized BclA into the basal layer. Free N-terminal residues are found in the mother cell cytoplasm. FIG. 10E illustrates that incorporation of the localized BclA proteins is almost complete, with subsequent increase in N-terminal peptides in the mother cell compartment. CLR is the collagen-like repeat domain of the BclA protein.

FIGS. 11A-11D show micrographs of a fusion of the entire BAS3290 ORF to the EGFP reporter under the control of the native BAS3290 σ$^K$ promoter. FIGS. 11A and 11B show late stage sporulating cells (T$_7$). FIGS. 11C and 11D show released spores. FIGS. 11B and 11D are bright field images of the spores or sporulating cells, respectively, whose fluorescence is shown in FIGS. 11A and 11C.

FIGS. 12A-12B show the pBT1744 construct (*B. anthracis* BclA N-terminal domain fused to EGFP) localized and attached to the spores of both *B. cereus* 14579 (FIG. 12A) and *B. thuringiensis kurstaki* (FIG. 12B).

FIG. 13A shows *B. anthracis* control spores. FIGS. 13A-13C are bright field images of the respective micrographs shown in FIGS. 13D-13F. FIGS. 13D-13F show binding (green) by all antibodies in sera following exposure to protein A-FITC conjugate.

FIGS. 14A-14D show the *B. thuringiensis* spores expressing the BclA NTD tagged PRRSV ORF5 labelled with immune sera (FIG. 14A) or preimmune sera (FIG. 14B) from pigs. FIGS. 14A and 14B are bright field images of the respective micrographs shown in FIGS. 14C and 14D that show binding (green) by all antibodies in sera following exposure to protein A-FITC conjugate.

FIG. 15 shows a SDS-PAGE western blot of the extracted proteins of the spore layers from the *B. thuringiensis* spores expressing the PRRSV ORF5 protein fused to the BclA protein from immune or preimmune pig sera. Lanes 1 and 3 shows wild type *B. thuringiensis*. Lanes 2 and 4 show the specific reactivity of the immune sera to the PRRSV ORF5 band. Lanes 1 and 2 are from preimmune pig sera, and lanes 3 and 4 are from PRRSV immune pig sera.

DETAILED DESCRIPTION

Figure 2B:
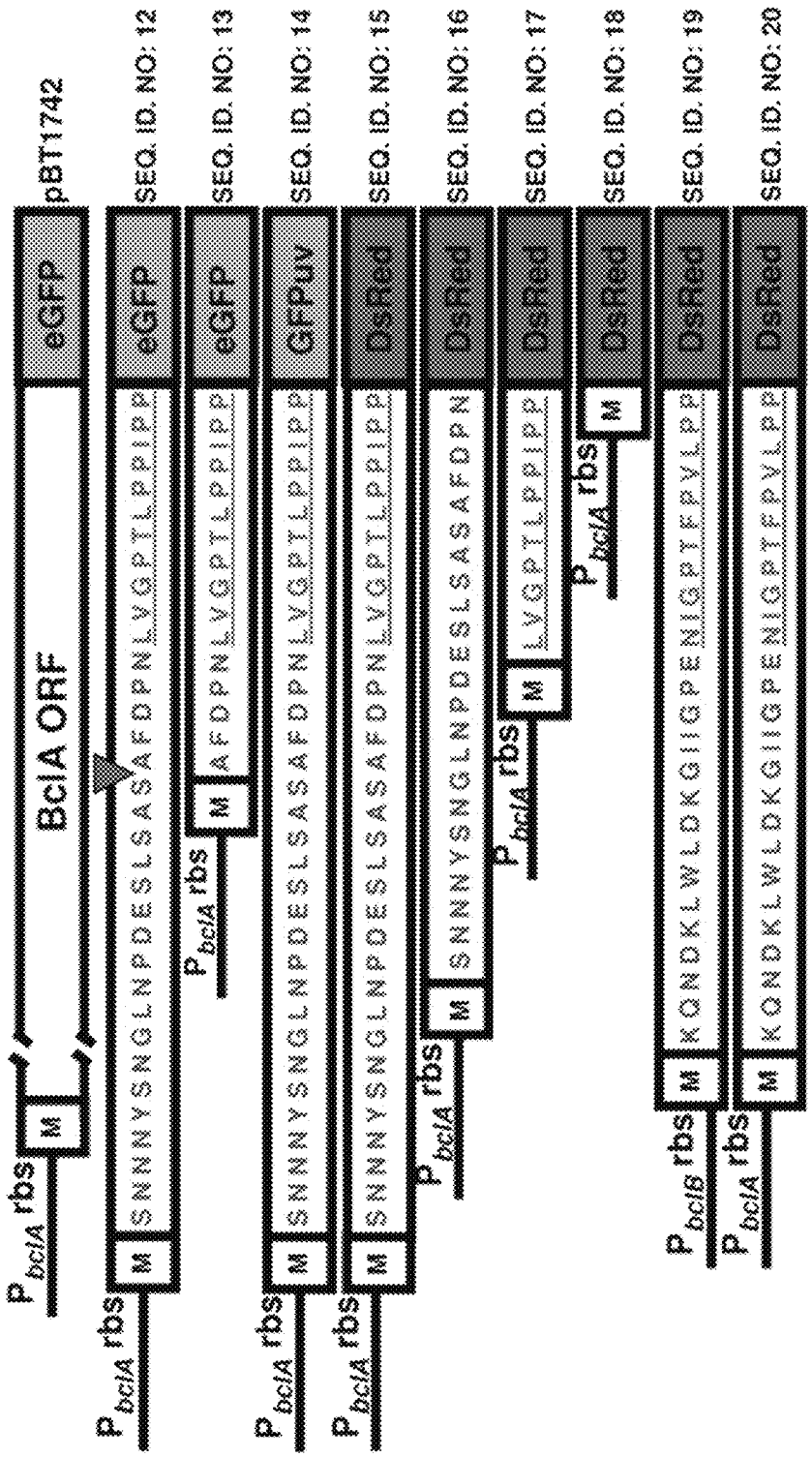
FIG. 2B diagrams the constructs described herein. Conserved regions are underlined. The arrow (▼) corresponds to the site of a previously described cleavage event. The designations of the corresponding fusion-encoding plasmids for the constructs are as follows: SEQ ID NO: 12 is pBT1744; SEQ ID NO: 13 is pBT1750; SEQ ID NO: 14 is pBT1693; SEQ ID NO: 15 is pBT1694; SEQ ID NO: 16 is pBT1701; SEQ ID NO: 17 is pBT1720; SEQ ID NO: 18 is pBT1729; SEQ ID NO: 19 is pBT1747; and SEQ ID NO: 20 is pBT1746.

The use of *Bacillus* endospores as a delivery vehicle has shown promise as a means of amplifying the magnitude and scope of the immune response to specific antigens. But, a procedure to efficiently localize foreign immunogenic proteins to the outer layers of exosporium-containing *Bacillus* spores has not been defined to date. Herein, are identified sequences of the BclA and BclB glycoproteins responsible for the insertion of these proteins into the exosporium layer of the spore. These sequences can be used as targeting domains to incorporate reporter proteins or antigens onto the spore surface. As such, herein is described a *Bacillus* exosporium antigen delivery (BEAD) system that provides a means to study the mechanisms of spore maturation in this important select agent pathogen. Furthermore, this novel delivery system can be exploited to incorporate foreign proteins into the exosporium of *B. cereus* family of bacteria, i.e. *B. anthracis*, *B. cereus*, and *B. thuringiensis*, resulting in the surface display of recombinant immunogens such as proteins or small molecules. In particular, the BEAD system described herein may be useful in combating exposure to pathogenic strains of *B. anthracis* by providing a means to deliver vaccines or other therapeutic compounds.

Identification of Domains Important in Protein Incorporation into the Exosporium Two collagen-like glycoproteins, BclA and BclB, have been shown to be surface exposed on spores of *B. anthracis*. The BclA and BclB are found in the exosporium layer of *B. anthracis* spores. The protein BclA is the major constituent of the surface nap and has been shown to be attached to the exosporium with its N terminus positioned at the basal layer and its C-terminus extending outward from the spore. BclA extracted from spores has been shown to lack its N-terminal 19 amino acids, which suggests that a proteolytic event is involved in the incorporation of this protein into the exosporium. The mechanisms by which BclA and BclB are incorporated into the exosporium are unknown. Herein, sequences at the N-terminus of these Bcl proteins that are sufficient for the incorporation of the proteins into the exosporium have been identified. Additional proteins are encoded in the *B. anthracis* genome with collagen-like triplet amino acid repeats. These determinants possess sequences resembling $\sigma^K$ promoter elements, and each is expressed during the sporulation phase of the *B. anthracis* life cycle. The N-termini of these proteins possess interesting sequence similarities (FIG. 2A).

The N-terminal domains of BclA and BclB allow for the targeting and incorporation of these proteins into the exosporium of *B. anthracis*. The BclA N-terminal domain comprises an 11 amino acid conserved motif, SEQ ID NO: 11, described herein and a 24 amino acid N-terminal region that contains a putative proteolytic cleavage site. A suggested role of the conserved motif is as a potential recognition site that leads to the positioning of the proteins to their appropriate target sites within the exosporium layer, but the attachment of proteins relies on more N-terminal sequences. Interestingly, addition of only 5 additional amino acids to the conserved motif (amino acids 20-24) allows for efficient localization and attachment of proteins, suggesting a role for those 5 amino acids in attachment of BclA to the exosporium. Removal of the conserved motif (but retention of the N-terminal amino acid sequence) leads to poor incorporation of the fusion proteins into the exosporium. The low level of incorporation observed may result from reduced positioning of the proteins at their sites of incorporation (limited fluorescence targeted to the exosporium of developing spores), but those proteins that are aligned properly get incorporated. The role of the proteolytic cleavage event has yet to be elucidated, but the data suggest that removal of the N-terminus prior to the putative cleavage site does not lead to a change in the level of protein incorporation into the exosporium. If a cleavage event is required for incorporation of BclA, the single methionine residue upstream of the cleavage site is sufficient for cleavage to occur. Alternatively, no cleavage event is required for exosporium incorporation and the cleavage event may be involved in release of the protein from the spore.

The process of assembly and attachment of BclA and BclB has not been described in detail to date. It is known that the BxpB (also called ExsFA) protein is involved directly or indirectly in the assembly of BclA on the surface of the exosporium, as bxpB mutant spores do not contain a BclA-coated nap. The N-terminal domains of BclA and BclB are responsible for the targeting and incorporation of these proteins into the exosporium of *B. anthracis*. FIGS. 10A-10E represent a model for the maturation and assembly of BclA into the exosporium. Production of BclA protein occurs early in sporulation, before the spore is visible within the mother cell by phase contrast microscopy (FIG. 10A). Soon thereafter, BclA localizes to the pole of the endospore facing the mother cell compartment (FIG. 10B). The BclA fusion protein begins to localize from the tip of the pole of the spore to encompass the newly formed exosporium basal layer around the spore (FIG. 10C). This localization is dependent on the presence of the conserved motif, amino acids 25-35 of BclA. Loss of this motif leads to greatly diminished BclA localization and subsequently poor incorporation. The pattern of initial exosporium development is consistent with previous studies, suggesting that exosporium assembly initiation is spatially regulated in the sporulating cell. This nap assembly pattern is presumably due to positioning of a protein or protein complex in the basal layer that recognizes the conserved motif in BclA. Fusions containing only the conserved motif localize to the mother cell center-facing pole of the spore. The motif only fusion localizes in a pattern following the newly formed basal layer across the spore, but this fusion is released at a time corresponding to the cleavage event. Because this fusion construct lacks the N-terminal cleavage site, it cannot be process and is not stably incorporated.

Maturation of the exosporium basal layer and the beginning of nap assembly occur at the same pole as that involved in the initiation of basal layer assembly. This initial localization of BclA is to an area smaller than the described 'cap, suggesting that the cap in exsY mutant spores results from a stalling in the progression of the exosporium development, rather than a broader initial deposition of BclA. It is proposed herein that the conserved domain is a localization domain that is recognized by an exosporium protein or complex that positions BclA for subsequent cleavage and incorporation.

Subsequent to positioning of BclA around the spore, cleavage of the N-terminal domain after residue 19 occurs concomitantly with stable incorporation of the protein into the exosporium (FIG. 10D). This cleavage event follows the localization of BclA around the spore from one pole to the other (FIG. 10E). Fusion constructs that contain a 'precleaved' N-terminus both localize and attach efficiently to the exosporium. This may indicate that the cleavage event per se is not required for the actual incorporation, but may create the proper substrate for the incorporation event. Studies are underway to determine if the N-terminal methionine residue is removed during incorporation, which would suggest a requirement for the proteolytic event.

Correct localization of the proteins in the exosporium driven by the N-terminal domain (NTD) alone suggests that recognition of the N-terminal sequence is key in the nap assembly process. Glycosylation of the collagen-like repeat region of BclA and the trimerization of the BclA protein owing to the presence of these repeats do not appear to be necessary for recognition and incorporation of BclA into the exosporium.

BclB is produced in lower quantities in the mother cell in comparison with BclA. Expression of BclB under the more active bclA promoter allows for incorporation of BclB fusions into the exosporium. However, the pattern of incorporation differs from the uniform distribution observed with the BclA fusions. Differences in the N-terminal amino acid sequences may result in interactions with a different set of exosporium proteins, which may account for the different localization results.

Exploitation of the Targeting Domains as a *Bacillus* Exosporium Antigen Delivery (BEAD) System During the sporulation process in *Bacillus*, spores are assembled with the outermost spore layers deposited last. The BclA glycoprotein is the predominant protein on the exosporium nap layer. This exosporium surface protein is expected to be among the last of the spore proteins to be incorporated into the spore. Data herein show that the N-terminal domains of the BclA and BclB proteins are sufficient for localization to the exosporium surface and that efficient expression on the spore surface is also dependent on the timing or levels of expression during sporulation. Amino acid sequences distal to the first 35 amino acids of the BclA protein are not required for surface localization on spores and can be replaced with foreign protein sequences or other small molecules that can be incorporated into fusions of the types described herein.

Use of the *Bacillus* exosporium antigen delivery (BEAD) system is expected to allow for high expression of foreign proteins or other small molecules in the endospore of *B. anthracis* and other BclA-containing *Bacillus* species (e.g. *B. cereus* and *B. thuringiensis*). The amount of incorporation surpasses that of recombinant proteins expressed on *B. subtilis* spores using the CotB/C systems. Advantageously, the ability of *B. anthracis* spores to illicit an immune response has been well characterized, and combining this ability with the inherent stability of the spores, provides a promising platform for the delivery of recombinant antigens or other small molecules.

The BEAD system has implications for the development of potentially better and safer vaccines against anthrax and other biothreat agents. Important immunogens, such as *B. anthracis* protective antigen, could be expressed on the surface of an anthrax spore or a spore from another *B. cereus* family member using any of the methods detailed herein. Herein, the BEAD system is demonstrated using well-known reporter proteins and a well-characterized antigen of viral origin. It is expected that any suitable antigen or small molecule may be recombined using the methods herein. Suitable antigens or small molecules are those that are known or expected to illicit a desired immune response that is sufficient to yield a therapeutic or protective effect when expressed on the exterior of a *Bacillus* spore. Suitability in large part will be determined by the folding in the three-dimensional structure once the recombinant antigen is incorporated into the exosporium, i.e. the antigenic portion(s) of the recombinant molecule must be available for detection by the immune system.

Preferably, spores used in the system are inactivated such that they cannot germinate. Exposure to ultraviolet (UV) radiation is a preferred method of inactivating spores; however, any of the compatible, inactivation methods known in the art may be used. Alternatively, spores derived from nontoxigenic strains, or genetically or physically inactivated strains, could be developed as part of a delivery system against anthrax. This system would provide the important protective antigen immunogen without the problems associated with residual toxicity and would have the additional advantage of providing spore-associated antigens that have been shown to provide enhanced protection against anthrax in animal models of infection. Furthermore, use of a recombinant spore as a delivery platform for therapeutic compositions provides adjuvant effects leading to both Th1 and Th2 immune responses, a feature not achieved with the current AVA vaccine. Lastly, expression of additional proteins, especially recombinant proteins, on the spore surface, for example; surface proteins from other biothreat agents, bacteria, viruses, or other pathogens could lead to the development of multivalent vaccines or therapeutic compositions against a variety of pathogens. Such vaccines or therapeutic compositions may suitable for use in man or animal.

Unless defined otherwise, all technical and scientific terms used herein have the same meaning as is commonly understood by one of skill in the art to which this invention belongs at the time of filing.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Experimental Procedures

Growth Conditions

*Bacillus anthracis* strain ΔSterne-1 was a gift from Dr. S. H. Leppla (National Institutes of Health, Bethesda, Md.). ΔSterne-1 is a strain derived from Sterne and lacks pXO1 and pXO2 (capsule- and toxin-negative). Sporulation was induced by growth on nutrient agar plates at 30° C. or in liquid culture using modified G Broth. Growth in liquid culture was monitored by absorbance at 600 nm. Sporulation was essentially complete (>95%) after 72 hours on nutrient agar plates. The degree of sporulation was assessed by phase contrast microscopy. Spores were harvested from 7-day old nutrient agar plates to ensure complete sporulation, washed 3 times in PBS, and stored at room temperature.

Creation of Fusion Constructs

Fusion constructs were created by polymerase chain reaction (PCR) amplification followed by splicing by overlapping extension as used in the art (see for example, Ho, et al., Gene 77: 51-59 (1989) and Horton, et al., Gene 77: 61-68 (1989)). Primers utilized in the PCR reactions are listed in Tables 1a and 1b. Correct fusions contained intact promoter regions including $\sigma^K$ elements, as well as native RBS and start codons. Fusion constructs were then subcloned into the shuttle plasmid pMK4 (see Sullivan et al., 1984), followed by electroporation into the ΔSterne strain of *Bacillus anthracis*. Selection of electrotransformed cells was on tryptic soy agar plates containing chloramphenicol at 10 µg/ml. Verification of the correct identify of the plasmids in the transformed cells was accomplished by antibiotic selection, followed by DNA extraction and plasmid DNA sequencing from vegetative cells.

TABLE 1a

Polymerase Chain Reaction Primers.

| Fusion | * | Primer 1 | DNA Sequence | SEQ. ID. NO. |
|---|---|---|---|---|
| pBT1744 | US | 106 | ctcgagtaatcaccctcttccaaatc | 21 |
|  | DS | 177 | ttaccaccgataccaccaatggtgagcaagggcgagg | 22 |
| pBT1742 | US | 106 | ctcgagtaatcaccctcttccaaatc | 23 |
|  | DS | 158 | ccattattattgaaaaagttgctatggtgagcaagggcgagg | 24 |
| pBT1750 | US | 106 | ctcgagtaatcaccctcttccaaatc | 25 |
|  | DS | 213 | ggaggtgaatttatggcatttgaccctaatcttg | 26 |

TABLE 1a-continued

Polymerase Chain Reaction Primers.

| Fusion | * | Primer 1 | DNA Sequence | SEQ. ID. NO. |
|---|---|---|---|---|
| pBT1758 | US | 106 | ctcgagtaatcaccctcttccaaatc | 27 |
|  | DS | 243 | aaggctgccgcagcgatgtcaaataataattattcaaatgaccatgat | 28 |
| pBT1693 | US | 106 | ctcgagtaatcaccctcttccaaatc | 29 |
|  | DS | 65 | ccaccgataccaccaatgagtaaaggagaagaacttttcac | 30 |
| pBT1694 | US | 106 | ctcgagtaatcaccctcttccaaatc | 31 |
|  | DS | 66 | ttaccaccgataccaccaatgaccatgattacgccaagcttg | 32 |
| pBT1729 | US | 106 | ctcgagtaatcaccctcttccaaatc | 33 |
|  | DS | 83 | acgctttatggaggtgaatttatgaccatgattacgccaagc | 34 |
| pBT1701 | US | 106 | ctcgagtaatcaccctcttccaaatc | 35 |
|  | DS | 94 | tcaaatggattaaaccccgatgaatctttatcagctagtgcatttgac cctaatatgaccatgattacgccaagcttgc | 36 |
| pBT1720 | US | 106 | ctcgagtaatcaccctcttccaaatc | 37 |
|  | DS | 92 | atgcttgtaggacctacattaccaccgataccaatgaccatgattacg ccaagcttgc | 38 |
| pBT1747 | US | 110 | ctcgagattagaacgtaaccaatttag | 39 |
|  | DS | 67 | accttcccggttcttcccccaatgaccatgattacgccaagcttg | 40 |
| pBT1746 | US | 106 | ctcgagtaatcaccctcttccaaatc | 41 |
|  | DS | 142 | acgctttatggaggtgaatttatgaaacagaatgacaaattatgg | 42 |

*: DS, downstream primer; US, upstream primer
US primer 1 corresponds upstream of the respective bclA or bclB promoter regions with associated XhoI sites.
US primer 2 corresponds to the end of the promoter or sequences in the NTD with an overlapping extension matching DS primer 1.
DS primer 1 corresponds with the 5p region of reporter genes (or NTDs fused to reporter genes for pBT1746, pBT1758).
DS primer 2 corresponds to the 3p region of reporter genes with associated XhoI sites.
pBT1746 was constructed by PCR amplification of construct pBT1747 (DS primers) followed by SOE to the bclA promoter region (US primers).
pBT1758 was constructed by PCR amplification of the pBT1693 construct with (DS primers) followed by SOE to the PCR product of the amplification of the US primers.

TABLE 1b

Polymerase Chain Reaction Primers.

| Fusion | * | Primer 2 | DNA Sequence | SEQ. ID. NO. |
|---|---|---|---|---|
| pBT1744 | US | 178 | cctcgcccttgctcaccattggtggtatcggtggtaa | 43 |
|  | DS | 157 | gcctcgagttacttgtacagctcgtccatgc | 44 |
| pBT1742 | US | 159 | cctcgcccttgctcaccatagcaacttttcaataataatgg | 45 |
|  | DS | 157 | gcctcgagttacttgtacagctcgtccatgc | 46 |
| pBT1750 | US | 214 | gattagggtcaaatgccataaattcacctccata | 47 |
|  | DS | 157 | gcctcgagttacttgtacagctcgtccatgc | 48 |
| pBT1758 | US | 244 | catcgctgcggcagccttgtacagctcgtccatgcc | 49 |
|  | DS | 103 | ctcgagttatttgtagagctcatccatgcc | 50 |
| pBT1693 | US | 100 | ttctcctttactcattggtggtatcggtggtaatgtaggtcc | 51 |
|  | DS | 103 | ctcgagttatttgtagagctcatccatgcc | 52 |
| pBT1694 | US | 101 | tggcgtaatcatggtcattggtggtatcggtggtaatgtagg | 53 |
|  | DS | 104 | ctcgagtaaaggaacagatggtggcgtccctcg | 54 |
| pBT1729 | US | 90 | caagcttggcgtaatcatggtcataaattcacctccataaagcgttc | 55 |
|  | DS | 104 | ctcgagtaaaggaacagatggtggcgtccctcg | 56 |
| pBT1701 | US | 95 | gctgataaagattcatcggggtttaatccatttgaataattattatttgac ataaattcacctccataaagcg | 57 |
|  | DS | 104 | ctcgagtaaaggaacagatggtggcgtccctcg | 58 |

TABLE 1b-continued

Polymerase Chain Reaction Primers.

| Fusion | * | Primer 2 | DNA Sequence | SEQ. ID. NO. |
|---|---|---|---|---|
| pBT1720 | US | 85 | tggtatcggtggtaatgtaggtcctacaagcataaattcacctccataaagcg | 59 |
|  | DS | 104 | ctcgagtaaaggaacagatggtggcgtccctcg | 60 |
| pBT1747 | US | 108 | tggcgtaatcatggtcattggggaagaaccgggaagg | 61 |
|  | DS | 104 | ctcgagtaaaggaacagatggtggcgtccctcg | 62 |
| pBT1746 | US | 143 | cataatttgtcattctgtttcataaattcacctccataaagcgt | 63 |
|  | DS | 104 | ctcgagtaaaggaacagatggtggcgtccctcg | 64 |

*Same footnote as Table 1a.

Spore Analysis by Flow Cytometry

Ten milligrams of spores were resuspended in 500 μl of 4% paraformaldehyde in PBS and incubated for 2 hours at room temperature. The spores were then washed four times with PBS and resuspended in StartingBlock (Pierce) and incubated with mixing at room temperature for 45 minutes. The spores were then pelleted and resuspended in Starting-Block. Rabbit polyclonal antiserum (1:250 dilution) against rBclA was then added and incubated with mixing at room temperature for 45 minutes. The spores were then washed three times in StartingBlock PBS and then incubated with mixing with FITC-Protein A conjugate (Sigma Chemical Co.) and incubated for 45 minutes at room temperature. The spores were then washed three times with StartingBlock, followed by two washes with PBS and then processed on a FACScan flow cytometer using a 488 nm argon laser (Beckton Dickinson Biosciences). Data were analyzed using Cell Quest analysis software (Beckton Dickinson).

Micrograph Images

Samples from sporulating cells on nutrient agar plates or in modified G broth were collected at indicated intervals and diluted in 10 μl of PBS containing DABCO (Diazabicyclooctane, Acros Organics) anti-fade reagent. All images were obtained using a Nikon E600 epi-fluorescence microscope using a 60× or 100× oil immersion objective.

Transmission Electron Microscopy

Immunogold labelling of embedded spores was performed after fixation of spores in a 2% glutaraldehyde and 2% formaldehyde PBS solution. Spores were embedded in 3% agar (EM Science, Gibbstown, N.J.). Dehydration involved sequential treatment with 25%, 50%, 75%, 95% and 100% acetone. Polymerization was carried out at 60° C. in Epon/araldite resin. Sections were cut at 85 nm thickness and put on 200-mesh carbon-coated copper grids; the cut grid sections were blocked in a 1% BSA solution for 30 min. The grids were washed three times in PBS, and the primary antibodies were added to the grids at a concentration of 1:25 in incubation buffer (Aurion). One hour later, the grids were washed six times in incubation buffer and incubated with 1:25 goat antirabbit secondary conjugated with 10 or 20 nm colloidal gold beads and allowed to bind for 2 hours. After a series of washes in PBS, the grids were post-fixed in 2% glutaraldehyde on 0.1 M PBS for 5 min and finished with washes in PBS and distilled water. Samples were examined with a JEOL 1200EX electron microscope.

Example 1: The BclA Protein Contains an N-Terminal Exosporium Targeting Domain

Given that the BclA protein associates with the exosporium via its N-terminus, this N-terminal conserved sequence, SEQ ID NO: 11 (see FIG. 2A), was investigated for the possible targeting of BclA and other collagen-like proteins to the exosporium.

To determine if the N-terminal domain of BclA is sufficient to target the native protein to the exosporium, two gene fusions were generated to the eGFP fluorescent reporter. PCR amplification of the upstream promoter/regulatory sequences of bclA and including the N-terminus coding sequence through the conserved motif or the entire bclA coding sequence was performed. These PCR products were then spliced with the eGFP reporter gene to produce in-frame fusions (FIG. 2B). The DNA constructs were subcloned into the pMK4 shuttle plasmid using known techniques (see Sullivan et al., 1984) and introduced into the plasmid-free ΔSterne strain of B. anthracis by electroporation. Transformants were either induced to sporulate in synchronized modified G Broth or grown in brain-heart infusion broth overnight and induced to sporulate by culturing on nutrient agar plates at 30° C. for 3 days. Expression of the reporters was examined by epi-fluorescence microscopy.

Figure 3O:
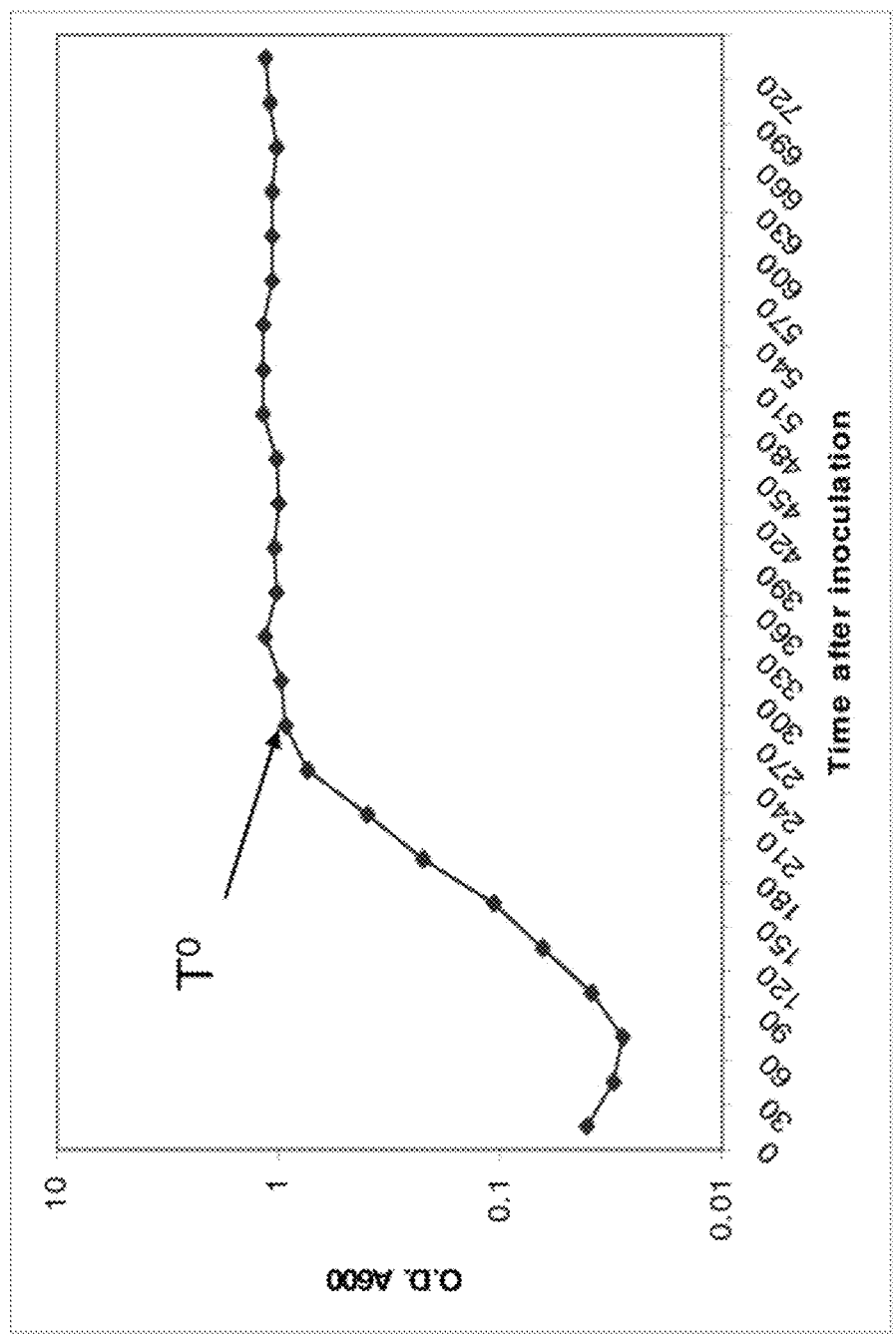

The transformed cells containing the BclA ORF fusion (pBT1742) or N-terminal domain (NTD) fusion (pBT1744) did not express the eGFP reporters during exponential growth (FIG. 3A), which is consistent with the known expression pattern shown by gene array analysis (see Bergman et al., 2006). As the cells expressing the fusions transitioned into stationary phase with the concomitant physiological shift to the sporulation process, fluorescence appeared throughout the mother cell cytoplasm (FIG. 3B). Two hours into stationary phase ($T_2$), BclA is expressed and translated, before a visible spore is formed in the mother cell (FIGS. 3B and 3G). The developing spore surface does not appear to be initially enriched for this reporter fusion protein during the early phases of visible spore development, with the emergent spore evident as a darkened area in the sporulating cell and with no enhanced fluorescence around the spore periphery (FIG. 3B). Synthesis of the fusion protein thus appears to be temporally distinct from incorporation into the exosporium. One hour later ($T_3$), a small amount of enhanced fluorescence became evident at one pole of the spore periphery (FIG. 3C). The initial polar localization of the BclA fusion was oriented towards the mother cell compartment, away from the pole of the mother cell, which is consistent with reports that the exosporium is initiated at this point (Ohye and Murrell, 1973; Steichen et al., 2007). As stationary phase progresses into the fourth hour ($T_4$), this area of fusion protein incorporation at one pole expands around the pole (FIG. 3D). At $T_6$, the exosporium is formed making its way around the spore (FIG. 3E), which was accompanied by a corresponding decrease in cytoplasmic fluorescence, presumably marking the incorporation of the fusion constructs into the exosporium (FIG. 3E). Shortly thereafter, at $T_7$, the incorporation of the fusion into the exosporium was complete. The cytoplasm of the mother cell lost its fluorescence while the surface of the spore retained fluorescence (FIG. 3K). This loss of cytoplasmic fluorescence presumably resulted from deposition of the protein on the spore surface, leakage of the fusion protein from the cell, degradation of the fusion protein or a combination of these events. Examination of the spores at 10 hours into stationary phase ($T_{10}$) revealed the presence of released, highly fluorescent spores (FIG. 3L). A representative growth curve is presented in FIG. 3O. $T_0$ denotes the point of entry into stationary phase.

For comparison, the BclA N-terminal domain fusion (pBT1744) was compared with a second constructed fusion consisting of the entire bclA open reading frame fused to the eGFP reporter gene (pBT1742, FIG. 2B). This fusion encoded by pBT1742 localized and attached to the spore surface at identical time points and distribution as the BclA N-terminal fusion encoded by pBT1744 (FIGS. 4A-4J). This result suggests that the N-terminal domain alone is sufficient for localization and incorporation of the BclA protein onto the spore surface.

Example 2: N-Terminal Amino Acids Required for Exosporium Incorporation

BclA released from spores lack its N-terminal 19 amino acids (Sylvestre et al., 2002; Steichen et al., 2003). It is unknown whether the proteolytic event resulting in the loss of these N-terminal residues takes place during exosporium assembly and BclA incorporation, or occurs after BclA has been stably inserted into the exosporium layer. To determine whether these initial N-terminal amino acids are required for efficient incorporation into the exosporium, a third fusion (pBT1750) was constructed, containing the bclA promoter region, RBS, through the bclA initiation codon followed by the coding sequence for amino acids 20-35 of BclA fused to the eGFP coding sequence (see FIG. 2B). This construct mimics the spore-extracted form of BclA (differing only by the presence of the N-terminal methionine residue), and allows for examination of the role of the truncated N-terminus in incorporation of BclA (FIG. 4K-4O). The pBT1750-expressing cells mirrored the pBT1742 and pBT1744 fusion cultures in their pattern of fluorescence incorporation and timing, suggesting that the initial 19 amino acids are not necessary for localization of BclA into the exosporium.

Figure 4P:
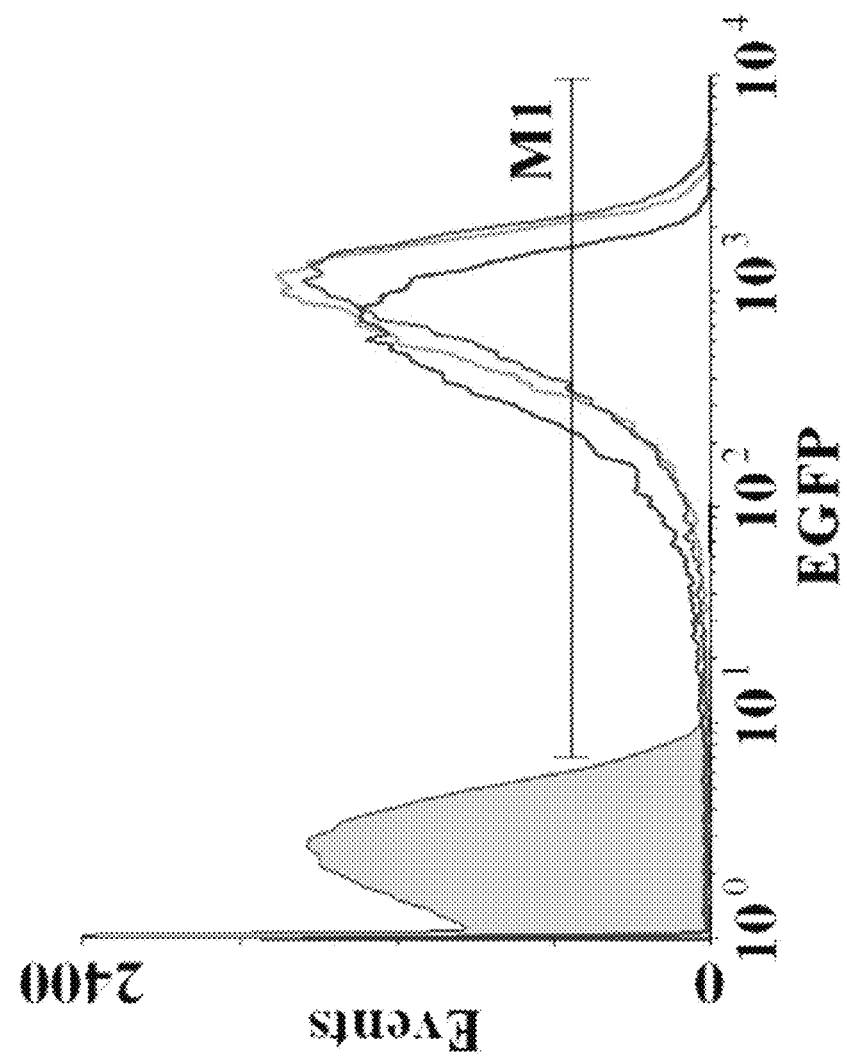
FIG. 4P is a histogram of the flow cytometry results for spores containing the pBT1744, pBT1742, and pBT1750 fusions. The gray area under the curve is the ΔSterne (pMK4) control spores. The green (greatest number of peak events, light gray) and purple (overlaps with green but slightly fewer peak events) lines correspond to the pBT1744 and pBT1742 fusions, respectively. The blue line (fewest peak events) represents the pBT1750 fusion.

To quantify the relative fusion incorporation levels, a direct comparison of the fluorescence associated with each spore type was undertaken by flow cytometry. All three fusions, (spores containing pBT1744, pBT1742, and pBT1750 fusions) localized to the spore surface to similar degrees (FIG. 4P). Greater than 97% of the spores for all three fusions were positive for fluorescence (Table 2). The mean positive fluorescence (MPF) for the purified, paraformaldehyde-fixed spores was 767 for pBT1744, 817 for pBT1742, and 528 for pBT1750. These data suggest that the N-terminal domain of BclA is not only sufficient, but as efficient as the intact BclA protein in targeting the reporter protein to the spore surface and its stable incorporation of the protein onto the spore. The loss of the N-terminal 19 amino acids did not greatly affect the incorporation of BclA, as only a modest decrease in the amount of fluorescence was seen in the pBT1750-containing spores.

TABLE 2

Fluorescence of Spores Determined by Flow Cytometry

| Designation | % Positive Spores Over Background | PMF | PMF Fold Increase |
|---|---|---|---|
| ΔSterne pMK4 | 5.5 | 7.42 | 1.0 |
| pBT1742 | 89.5 | 140.9 | 19.0 |
| pBT1744 | 99 | 307.9 | 41.5 |
| pBT1693 | 98.3 | 59.69 | 8.0 |
| ΔSterne pMK4 | 3.9 | 5.5 | 1.0 |
| pBT1694 | 96.6 | 94.6 | 17.2 |
| pBT1729 | 3.8 | 5.7 | 1.0 |
| pBT1701 | 73.2 | 15.2 | 2.8 |
| pBT1720 | 11.4 | 6 | 1.1 |
| pBT1747 | 4.2 | 5.9 | 1.1 |
| pBT1746 | 72.5 | 16 | 2.9 |

Example 3: Cleavage of the N-Terminal Domain Associates with Incorporation of BclA into the Exosporium The attachment of the pBT1750-encoded fusion implied that the truncated BclA can be recognized and attached to the exosporium. To address the question of whether cleavage of the intact BclA N-terminal domain occurs during exosporium formation, a dual reporter fusion construct was made. The pBT1758-encoded fusion consists of the bclA promoter followed by the mCherry monomeric reporter gene (Shaner et al., 2005; Giepmans et al., 2006) fused in frame to the BclA N-terminal domain that was in turn fused in frame to the GFPuv reporter (FIG. 5A). This fusion allows for the analysis of cleavage in the N-terminal domain (NTD) by appearance of separation between the red fluorescence and green fluorescence of the reporter proteins.

Similar to the findings with the single-reporter fusions, the pBT1758 fusion appeared in the mother cell cytoplasm prior to the appearance of the emerging spore (FIGS. 5B and 5H). The orange fluorescence (rather than yellow) likely resulted from a more intense red fluorescence of the mCherry fusion relative to monomers of the green GFPuv reporter protein in this fusion (Shaner et al., 2005). Soon thereafter, the fusion localized to the spore periphery, as demonstrated by the orange rings, localizing around the pole of the emerging spore (FIGS. 5C and 5I). At subsequent time points, the developing orange fluorescence continued to envelop the spore, followed by the putative cleavage event. This cleavage event results in the release of bound mCherry and subsequent emergence of a green spore (FIGS. 5D, 5E, 5J and 5K). The reduction in the local concentration of mCherry, combined with the enrichment of GFPuv fluorescence at the spore periphery resulted in production of yellow fluorescence (FIGS. 5D, 5E, 5J and 5K). Progression of cleavage around the spore surface released increasing concentrations of the mCherry reporter with the NTD 19-amino-acid tail attached to its C-terminus into the mother cell cytoplasm. However, the GFPuv reporter, by virtue of its attachment to the C-terminus of BclA amino acids 20-35, became stably attached to the spore surface (FIGS. 5E and 5F). Completion of the cleavage events (yellow fluorescence reaching the distal pole of the spore) coincided with the definitive appearance of the spore in the bright field images (FIGS. 5E and 5K). The cleavage events trailed the positioning of BclA at the exosporium (as demonstrated in FIGS. 3A-3O) from the mid-mother cell-facing pole of the spore to its completion at the opposite pole (FIGS. 5E and 5K). Fluorescence of the released mCherry reporter quickly faded, as the cleaved mCherry fusion protein appeared either to be unstable inside the mother cell, or was rapidly lost from the cytoplasm during initial stages of mother cell lysis (FIGS. 5F and 5L). The released spores retained their incorporated green fluorescence (FIGS. 5G and 5M).

The systematic cleavage of the reporter fusions at the site of the exosporium assembly demonstrated the difference in timing between the positioning of the BclA protein at the exosporium and the cleavage event. No discernable red or orange fluorescence was observed in the released spores, demonstrating a correlation of the cleavage event with the final incorporation of BclA into the exosporium. Therefore, the loss of the N-terminal residues of BclA results from events related to exosporium synthesis and not subsequent release of BclA.

Example 4: Reporter Oligomerization is not Required for Exosporium Incorporation The interwinding of the individual native BclA molecules to form a triple helix in wild-type spores is made possible by interactions among the C-terminal domains of the BclA monomers (Boydston et al., 2005). The ability of pBT1744 and pBT1750 fusions, lacking both the C-terminal domain of BclA and the collagen-like region (CLR) with its associated glycosylation sites (Daubenspeck et al., 2004), to localize to the exosporium suggests that neither oligomerization of proteins nor glycosylation of the CLR are essential for incorporation of proteins into the exosporium of *B. anthracis*. Although not essential, oligomerization of proteins may be beneficial in localization to the exosporium. Two additional constructs were made that contained the BclA protein sequence from pBT1744, but fused to the GFPuv reporter (pBT1693) or DsRed (pBT1694, FIG. 2B). The GFPuv reporter has a natural propensity to dimerize under physiological conditions, and the DsRed reporter protein obligately tetramerizes (Yang et al., 1996; Baird et al., 2000). The pBT1693 and pBT1694 constructs (FIGS. 6A-6J) displayed expression kinetics and fluorescent distribution profiles similar to the eGFP fusions (FIGS. 3A-3O and 4A-4P). In all cases, fluorescence appeared initially after sporulation had commenced followed by an increased concentration of the fluorescent reporter around the spore periphery (FIGS. 6A-6C, 6F-6H). The complete loss of cytoplasmic fluorescence in the pBT1694-containing sporulating cells prior to spore release may signify a more complete incorporation of the fusion proteins into the exosporium. A delay in the spore release of the pBT1694-encoded fusion cells was observed. The DsRed self-association of this tetramerizing protein (Baird et al., 2000) may form a tight shell around the spores and mask structures or interfere with natural processes that trigger spore release from the mother cells. After lysis of the mother cells, released spores retained surface-associated fluorescence (FIGS. 6D, 6E, 6I, and 6J).

To eliminate the possibility that the reporter proteins bind non-specifically to the exosporium, a control fusion was constructed. DsRed was expressed under the control of the bclA promoter and ribosome binding site (RBS) but without any of the bclA N-terminal coding sequence (pBT1729; FIG. 2B). Although containing identical promoter and RBS elements as the aforementioned constructs, the pBT1729-containing cells exhibited diminished fluorescence in the cytoplasm, suggesting that the DsRed protein without the N-terminal BclA sequence had a substantially shorter half-life in the sporulating cells. A similar observation was made with the mCherry reporter (a derivative of DsRed) of the pBT1758 fusion (FIGS. 5A-5M). However, the DsRed in the pBT1729-containing cells did not concentrate around the periphery of the spore (FIGS. 6K-6M) and the released spores were not fluorescent (FIGS. 6N and 6O). Thus, the labelling of the spores by the reporter fusions appeared not to be the result of non-specific binding of the reporter proteins to the spore surface.

Example 5: Contributions of the Conserved Motif and N-Terminal Sequences to Exosporium Incorporation of Reporter Proteins To determine if the conserved motif sequence identified in FIG. 2A was required for attachment of the fusion proteins to the spore surface, fusion constructs were created that either contained the BclA N-terminal sequence lacking the conserved sequence (SEQ ID NO: 11; pBT1701), or contained only the conserved motif, SEQ ID NO: 11, fused to DsRed (pBT1720, FIG. 2B). The pBT1701-encoded fusion protein without the conserved motif exhibited a reduced concentration around the spore periphery, no polar localization, and maintained cytoplasmic fluorescence up to the time of spore release. Only modest levels of fluorescence were detected on released spores (FIGS. 6P-6T). Thus loss of the conserved N-terminal BclA sequence resulted in a diminished exosporium incorporation of the fusion protein.

The pBT1720-encoded fusion protein, consisting of the conserved motif alone fused to DsRed, but lacking the rest of the BclA initial N-terminal residues (residues 2-24, which includes the proteolytic cleavage site), concentrated around the spore periphery quickly after being expressed with a corresponding decrease in cytoplasmic fluorescence. However, released spores were devoid of fluorescence (FIGS. 6U-6Y). Thus the presence of only the conserved motif resulted in the fusion protein being targeted to the spore periphery, but was insufficient to allow attachment of the protein to the mature exosporium. It was observed that localization of the motif-only fusion followed the normal progression of NTD localization observed with the pBT1744-encoded fusion (mother cell proximal pole to the mother cell distal pole), but stable incorporation failed to occur and the fusion was lost from the spores (FIGS. 6U-6W). The BclA N-terminal 24 amino acids missing in this fusion protein contain the site for the proteolytic cleavage event that may be involved in the attachment of BclA to the exosporium. Optimal localization and attachment of BclA to the maturing exosporium is dependent upon the conserved motif, whereas the ultimate attachment of BclA requires the N-terminal cleavage event.

Figure 7:
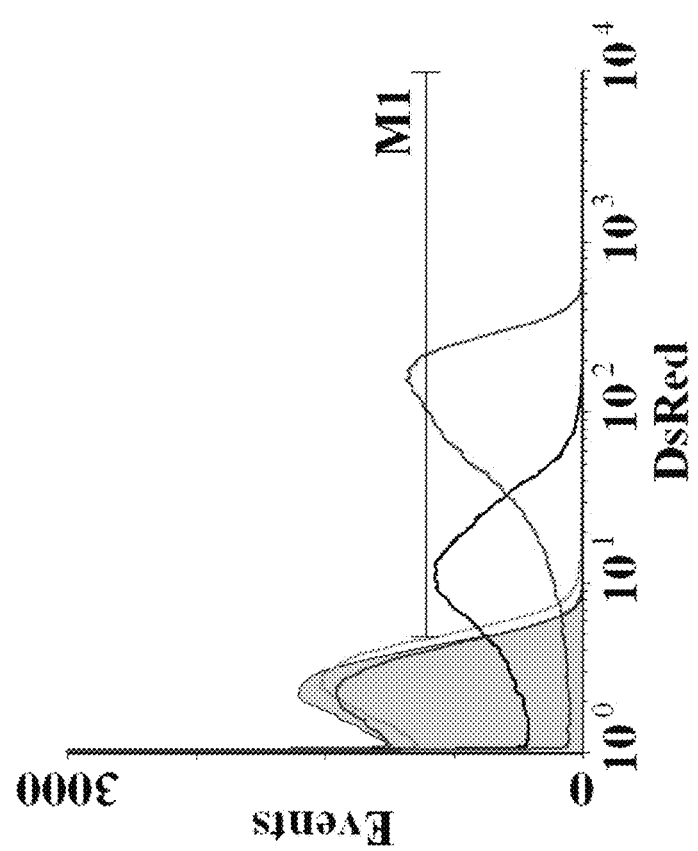
FIG. 7 shows flow cytometry histograms of the fusion constructs. The gray area represents ΔSterne (pMK4)-negative control spores. The red and black lines (both peak outside of the gray area, the red line peaks above M1 and the black line peaks below M1) represent spores containing the pBT1694- and pBT1701-encoded fusions, respectively. The orange (light gray, mostly within the gray area) and dark green (entirely within gray area) lines represent spores containing the pBT1720- and pBT1729-encoded fusions, respectively.

To quantify the level of incorporation of each of the DsRed-containing fusion constructs into the released spores, flow cytometry was performed on purified, paraformaldehyde-fixed spores (FIG. 7 and Table 2). The DsRed fluorescence of the spores bearing the intact BclA Nterminal 35 amino acid sequence (pBT1694) was 6.2-fold greater than all other DsRed-containing fusion constructs (FIG. 7). The fusion lacking the conserved motif (pBT1701) was detectably fluorescent, with greater than 73.2% of the spores positive over background and with a mean positive fluorescence (MPF) of 15.2. But these values were substantially lower than those obtained with pBT1694-bearing spores (96.6%, MPF 94.6%). The pBT1720 conserved motif-only fusion gave little detectable fluorescence above that of the negative control spores (11.4% to 3.9%, MPF 6). Spores from cells expressing DsRed without BclA N-terminal residues (pBT1729) were not detectably fluorescent over background (3.8% vs. 3.9%).

Example 6: Exosporium Incorporation Utilizing the BclB N-Terminal Domain

After establishing that the BclA N-terminal domain was sufficient to localize proteins to the spore periphery, the ability of the corresponding BclB domain to target proteins to the exosporium was studied. The DsRed reporter was fused to the BclB N-terminus with the coding sequence up to and including the conserved region, with the natural bclB promoter and RBS (pBT1747; FIG. 2B). Previous reports have suggested that bclB and bclA are transcribed at an identical stage in sporulation, but with bclB transcribed at a –2-fold lower level (Bergman et al., 2006). However, the pBT1747-encoded fusion appeared earlier in the sporulation process than the BclA fusions and at a greatly reduced level, lower than the reported 2-fold difference in mRNA (Bergman et al., 2006). Released spores only contained barely detectable levels of the fusion protein (FIG. 8G).

To increase production of the BclB fusion proteins, the BclB N-terminal sequence fused to DsRed was positioned under the control of the more active bclA promoter and RBS elements (pBT1746; FIG. 2B). The pBT1746-encoded fusion protein was expressed at a level similar to that of the pBT1694 construct. The pBT1746-encoded BclA construct mimicked the pBT1694-encoded BclA construct, with both fluorescent fusions produced and localizing around the spore periphery before release of the fluorescent spores (FIGS. 8A-8F). There appeared to be a difference in the spore localization pattern on the pBT1746-encoded fusion, with the fluorescence spread across the spore in a slightly mottled fashion and ultimately encompassed only 75% of the spore, with one pole devoid of fluorescence (FIGS. 8E and 8F). The fusion did not exhibit the more uniform distribution seen with the pBT1693- and pBT1694-encoded fusions. Although incorporation was evident, the capacity of the BclB domain to target proteins to the spore surface was reduced when compared to that of the BclA N-terminal fusion (FIG. 8G). The pBT1746-encode BclB fusion spores were 72.5% positive compared with 96.6% for pBT1694-containing spores, with a MPF of 16.1 compared to 94.6. This result illustrates that the presence of the BclB N-terminus is sufficient to localize foreign proteins to the spore surface, but the degree of incorporation is dependent upon the production level of the protein and/or the differences in the sequences of the N-terminus or targeting domains of BclA and BclB.

Example 7: Native BclA is Incorporated into Spores Expressing Reporter Proteins To determine if native BclA continued to be incorporated into the exosporium in cells expressing the Bcl-domain-containing fusions, fluorescent purified spores were incubated with rabbit anti-recombinant BclA polyclonal antibodies followed by FITC-Protein A conjugate (FIGS. 9A-9F). Spores from each of the DsRed fusion constructs retained the ability to bind anti-BclA antibodies, indicating that native BclA was incorporated into the spores. Spores from the promoter-only constructs (pBT1720 and pBT1729) produced spores with wild-type levels of BclA as expected (FIGS. 9D, 9E). Spores with the fusion protein incorporated into the exosporium demonstrated a pronounced heterogeneity in the amount of fusion protein on the spore surfaces relative to the native BclA levels in individual spores in the population (FIG. 9A-9F). This result was especially noticeable in the pBT1746-encoded (BclB NTD) fusion, suggesting that the incorporation of the fusion hinders native BclA incorporation or may effect the topology of the proteins, thus inhibiting binding or access of the anti-BclA polyclonal antibodies to the native BclA.

Example 8: Incorporation of Fusion Proteins onto the Exosporium Surface

Exosporium targeting was checked by immune-electron microscopy analysis of spores containing the pBT1744-encoded BclA N-terminal fusion to eGFP. Spores were analysed under TEM after treatment with either anti-rBclA rabbit polyclonal antibodies or anti-GFP rabbit polyclonal antibodies (Imgenex). These primary antibodies were followed with secondary gold-labelled anti-rabbit antibodies bearing 20 and 10 nm gold particles, respectively (FIGS. 9G and 9H). Both anti-GFP and anti-rBclA antibodies localized to the nap layer of the exosporium. The anti-GFP antibodies were found in closer proximity to the basal layer, which may be due to the eGFP protein lacking the filamentous structure associated with native BclA. There was no indication that the incorporation of the fusion proteins differed from the incorporation of natural BclA. The appearance of the exosporium was normal, despite the incorporation of the fusion proteins.

Example 9: The BAS3290 Protein can be Used to Introduce Foreign Antigens

The BAS3290 protein of *B. anthracis* is predicted to localize to the exosporium due to the high degree of identity of its N-terminal domain (SEQ ID NO: 8) to the N-terminal domain of the localization domain of the BclA protein (SEQ ID NO: 7; 13 of 14 amino acid residues identical). A fusion of the entire BAS3290 ORF to the EGFP reporter under the control of the native BAS3290 $\sigma^K$ promoter was constructed. This fusion protein was produced late in the sporulation process, which was consistent with transcription under this promoter. This fusion protein was produced and localized immediately to the exosporium (FIGS. 11A and 11B). After localization to the exosporium, this fusion was affixed to the released spores demonstrating as fluorescent spores (FIGS. 11C and 11D). This result demonstrates that the BAS3290 protein acts mechanistically similar to the BclA protein, and could also be utilized for the creation of fusion for surface display of foreign antigens on the exosporium of *B. anthracis*.

Example 10: Other Exosporium Containing-*Bacillus* Species

To demonstrate the conserved nature of the localization machinery in the *Bacillus cereus* family, the pBT1744 construct (*B. anthracis* BclA N-terminal domain fused to EGFP; see Thompson et al. 2008) was utilized. This pBT1744 construct was electroporated into *B. cereus* strain 14579 and *B. thuringiensis* strain *kurstaki*. Proper antibiotic resistant clones were allowed to enter sporulation, and observed upon release of free spores. The *B. anthracis* BclA N-terminal domain localized and attached to the spores of both *B. cereus* (FIG. 12A) and *B. thuringiensis* (FIG. 12B). This result demonstrates that any of the *Bacillus cereus* family may be used to incorporate foreign antigens onto exosporia of the family.

Example 11: *Bacillus* Exosporium Antigen Delivery (BEAD) Systems

Figure 13A:
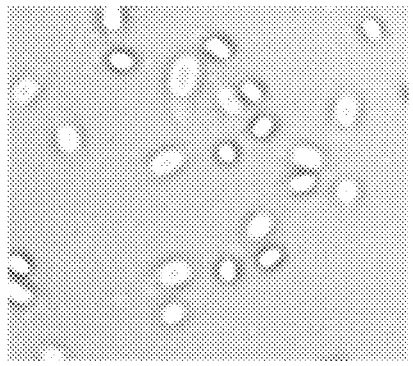
FIGS. 13A-13F show the *B. anthracis* spores expressing the BclA (FIG. 13B) and BclB (FIG. 13C) NTD tagged Porcine Respiratory and Reproductive Virus (PRRSV) ORF5 labelled with preimmune or immune sera from pigs.
Figure 13B:
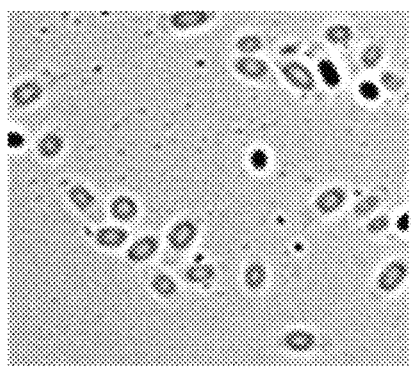
Figure 13C:
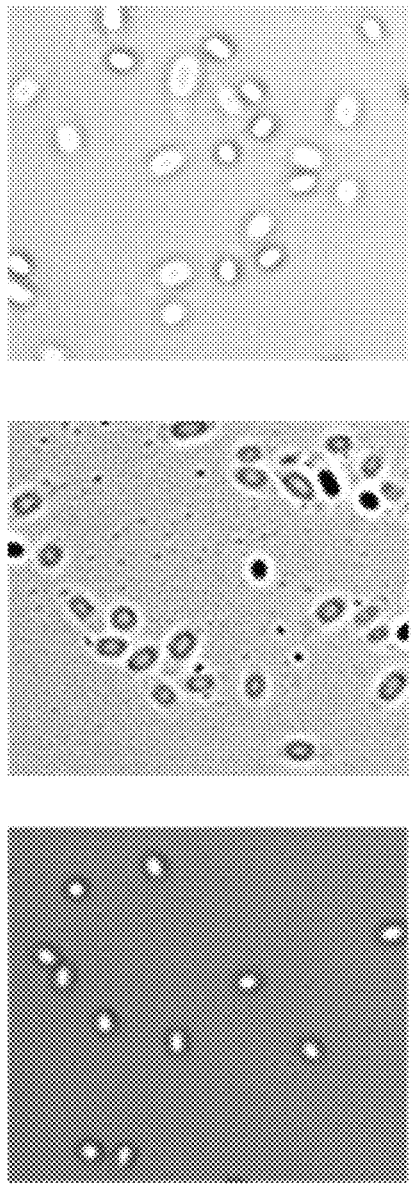
Figure 13D:
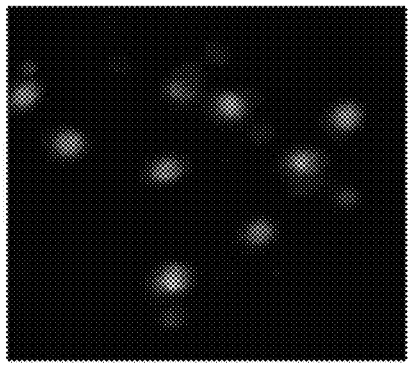
Figure 13E:
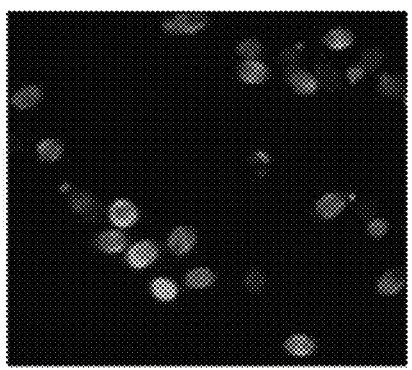
Figure 13F:
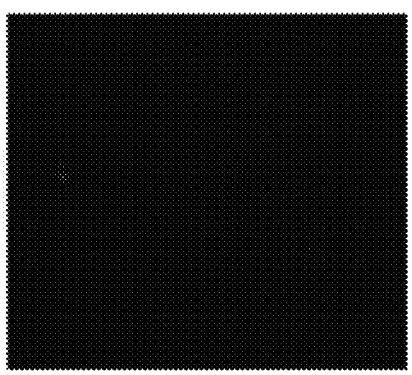

The ORF5 from the Porcine Respiratory and Reproductive Virus (PRRSV), which encodes a protective, neutralizing protein, was chosen to be an exemplary foreign antigen expressed using the BEAD system in different *Bacillus cereus* family members. Polymerase chain reaction (PCR) of the PRRSV ORF5 was accomplished using standard techniques. Fusion of the PRRSV ORF5 to the N-terminal domain of BclA or BclB was accomplished by splicing and overlapping extension techniques well-known in the art. Correct fusions were cloned into the shuttle plasmid pMK4, sequenced, and electroporated into *B. anthracis* strain ΔSterne and *B. thuringiensis* strain *kurstaki*. Correct transformants were selected, grown in Brain Heart Infusion broth and then allowed to sporulate by plating onto N agar plates at 30° C. Free spores were collected after 3 days, and washed with PBS to remove vegetative cell debris. Purified spores were then subjected to immunolabeling with sera from either preimmune pigs, or from pigs previously infected with PRRSV and to whom a known titer to PRRSV had been established. Exposure to sera was followed with protein A-FITC conjugate, which binds to all antibodies and lights up green. As shown in FIGS. 13A-13F, the *B. anthracis* spores expressing either the BclA or the BclB N-terminal domain (NTD) tagged PRRSV ORF5 labeled with immune sera (FIGS. 13B, 13C), while immune sera did not react with wildtype spores (FIG. 13A).

In *B. thuringiensis*, the BclA NTD tagged PRRSV ORF5 localized to the exosporium, but mostly preferentially to one pole (FIG. 14A). These spores did not react with the preimmune pig sera, suggesting the reactivity seen at the poles was specific to PRRSV (FIG. 14B). These results demonstrate that foreign antigens can be expressed on the surface of the exosporium of the *B. cereus* family members with this antigen expression system, and that reactivity to these proteins is demonstrated by immunofluorescence assays. This reactivity indicates that the foreign antigens have surface exposure and are available to stimulate an immune reaction.

Figure 15:
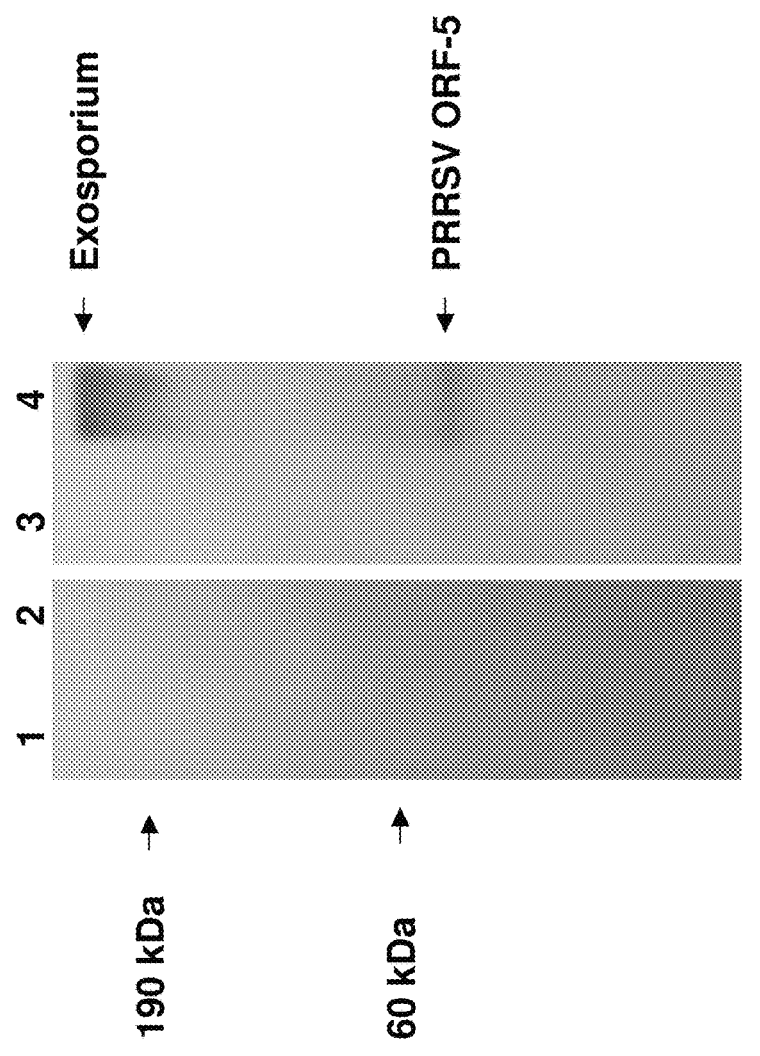

Next, extraction of the spore layers from the *B. thuringiensis* spore expressing the PRRSV ORF5 protein fused to the BclA protein was undertaken. Separation of these extracted proteins by SDS-PAGE, followed by western blotting with immune and preimmune pig sera (FIG. 15) further demonstrates the specific reactivity of the immune sera to the PRRSV ORF5 (see Lane 4 on the gel). The high molecular weight material on the western is indicative of large molecular weight exosporium complexes which do not dissociate under SDS or urea buffer insult. Glycosylation of these complexes leads to the variable molecular weight smear seen on the blot (Lane 4). The lower molecular weight band (Lane 4) corresponds to the molecular weight of the fusion of PRRSV ORF5 fused to BclA NTD.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the following claims.

REFERENCES

The following references, to the extent that they provide exemplary procedural or other details supplementary to those set forth herein, are specifically incorporated herein by reference. All patents and publications referred to herein are incorporated by reference.

Baillie, L., Hibbs, S., Tsai, P., Cao, G. L., and Rosen, G. M. (2005) Role of superoxide in the germination of *Bacillus anthracis* endospores. FEMS Microbial. Lett. 245: 33-38.

Baird, G. S., Zacharias, D. A., and Tsien, R. Y. (2000) Biochemistry, mutagenesis, and oligomerization of DsRed, a red fluorescent protein from coral. Proc. Natl. Acad. Sci USA 97: 11984-11989.

Barnes, A. G., Cerovic, V., Hobson, P. S., and Klavinskis, L. S. (2007) *Bacillus subtilis* spores: a novel microparticle adjuvant which can instruct a balanced Th1 and Th2 immune response to specific antigen. Eur. J. Immunol. 37: 1538-1547.

Basu, S., Kang, T. J., Chen, W. H., Fenton, M. J., Baillie, L., Hibbs, S., and Cross, A. S. (2007) Role of *Bacillus anthracis* spore structures in macrophage cytokine responses. infect Immun. 75: 2351-2358.

Bergman, N. H., Anderson, E. C., Swenson, E. E., Niemeyer, M. M., Miyoshi, A. D., and Hanna, P. C. (2006) Transcriptional profiling of the *Bacillus anthracis* life cycle in vitro and an implied model for regulation of spore formation. J. Bacterial. 188: 6092-6100.

Boydston, J. A., Chen, P., Steichen, C. T., and Turnbough, C. L. Jr. (2005) Orientation within the exosporium and structural stability of the collagen-like glycoprotein BclA of *Bacillus anthracis*. J. Bacteriol. 187: 5310-5317.

Boydston, J. A., Yue, L., Kearney, J. P., and Turnbough, C. L. Jr. (2006) The ExsY protein is required for complete formation of the exosporium of *Bacillus anthracis*. J. Bacterial. 188: 7440-7448.

Brossier, F., Levy, M., and Mock, M. (2002) Anthrax spores make an essential contribution to vaccine efficacy. Infect. Immun. 70: 661-664.

Ciabattini, A., Parigi, R., Isticato, R., Oggioni, M. R., and Pozzi, G. (2004) Oral priming of mice by recombinant spores of *Bacillus subtilis*. Vaccine. 22:4139-4143.

Chakrabarty, K., Wu, W., Booth, J. L., Duggan, E. S., Coggeshall, K. M., and Metcalf, J. P. (2006) *Bacillus anthracis* spores stimulate cytokine and chemokine innate immune responses in human alveolar macrophages through multiple mitogen-activated protein kinase pathways. Infect Immun. 74: 4430-4438.

Daubenspeck, J. M., Zeng, H., Chen, P., Dong, S., Steichen, C. T., Krishna, N. R., Pritchard, D. G., and Turnbough, C. L. Jr. (2004) Novel oligosaccharide side chains of the collagen-like region of BclA, the major glycoprotein of the *Bacillus anthracis* exosporium. J. Biol. Chem. 279: 30945-30953.

Driks, A. (2002) Maximum shields: the assembly and function of the bacterial spore coat. Trends Microbial. 10: 251-254.

Duc, L. H, Hong, H. A., Atkins, H. S., Flick-Smith, H. C., Durrani, Z., Rijpkema, S., Titball, R. W., and Cutting, S. M. (2007) Immunization against anthrax using *Bacillus subtilis* spores expressing the anthrax protective antigen. Vaccine 25: 346-355.

Duc, L. H., Hong, H. A., Fairweather, N., Ricca, E., and Cutting, S. M. (2003) Bacterial spores as vaccine vehicles. Infect. Immun. 71: 2810-2818.

Giorno, R., Bozue, J., Cote, C., Wenzel, T., Moody, K. S., Mallozzi, M., Ryan, M., Wang, R., Zielke, R., Maddock, J. R., Friedlander, A., Welkos, S., and Driks, A. (2007) Morphogenesis of the Bacillus anthracis spore. J. Bacterial. 189: 691-705.

Hachisuka, Y., Kojima, K., and Sato, T. (1966) Fine filaments on the outside of the exosporium of Bacillus anthracis spores. J. Bacterial. 91: 2382-2384.

Haldenwang, W. G. (1995) The sigma factors of Bacillus subtilis. Microbial. Rev. 59: 1-30.

Henriques, A. O., and Moran, C. P. Jr. (2007) Structure, assembly, and function of the spore surface layers. Ann. Rev. Microbial. 61: 555-588.

Hilbert, D. W., and Piggot, P. J. (2004) Compartmentalization of gene expression during Bacillus subtilis spore formation. Microbial Mol. Biol. Rev. 68: 234-262.

Ho, S. N., Hunt, H. D., Horton, R. M., Pullen, J. K., and Pease, L. R. (1989) Site-directed mutagenesis by overlap extension using the polymerase chain reaction. Gene 77: 51-59.

Horton, R. M., Hunt, H. D., Ho, S. N., Pullen, J. K., and Pease, L. R. (1989) Engineering hybrid genes without the use of restriction enzymes: gene splicing by overlap extension. Gene 77: 61-68.

Isticato, R., Cangiano, G., Tran, H. T., Ciabattini, A., Medaglini, D., Oggioni, M. R., De Felice, M., Pozzi, G., and Ricca, E. (2001) Surface display of recombinant proteins on Bacillus subtilis spores. J. Bacterial. 183: 6294-6301.

Kramer, M. J., and Roth, I. L. (1968) Ultrastructural differences in the exosporium of the Sterne and Vollum strains of Bacillus anthracis. Can J. Microbial. 14: 1297-1299.

Little, S. F., and Knudson, G. B. (1986) Comparative efficacy of Bacillus anthracis live spore vaccine and protective antigen vaccine against anthrax in the guinea pig. Infec. Immun. 52: 509-512.

Mauriello, E. M., Duc, L. H., Isticato, R., Cangiano, G., Hong, H. A., De Felice, M., Ricca, E., and Cutting, S. M. (2004) Display of heterologous antigens on the Bacillus subtilis spore coat using CotC as a fusion partner. Vaccine 22: 1177-1187.

Paccez, J. D., Nguyen, H. D., Luiz, W. B., Ferreira, R. C., Sbrogio-Almeida, M. E., Schuman, W., and Ferreira, L. C. (2007) Evaluation of different promoter sequences and antigen sorting signals on the immunogenicity of Bacillus subtilis vaccine vehicles. Vaccine 25: 4671-4680.

Raines, K. W., Kang, T. J., Hibbs, S., Cao, G. L., Weaver, J., Tsai, P., Baillie, L., Cross, A. S., and Rosen, G. M. (2006) Importance of nitric oxide synthase in the control of infection by Bacillus anthracis. Infect. Immun. 74: 2268-2276.

Redmond, C., Baillie, L. W., Hibbs, S., Moir, A. J., and Moir, A. (2004) Identification of proteins in the exosporium of Bacillus anthracis. Microbial. 150: 355-363.

Steichen, C., Chen, P., Kearney, J. P., and Turnbough, C. L. Jr. (2003) Identification of the immunodominant protein and other proteins of the Bacillus anthracis exosporium. J. Bacterial. 185: 1903-1910.

Steichen, C. T., Kearney, J. P., and Turnbough, C. L. Jr. (2005) Characterization of the exosporium basal layer protein BxpB of Bacillus anthracis. J. Bacterial. 187: 5868-5876.

Sullivan, M. A., Yasbin, R. E., and Young, F. E. (1984) New shuttle vectors for Bacillus subtilis and Escherichia coli which allow rapid detection of inserted fragments. Gene 29: 21-26.

Sylvestre, P., Couture-Tosi, E., and Mock, M. (2002) A collagen-like surface glycoprotein is a structural component of the Bacillus anthracis exosporium. Mol. Microbial. 45: 169-178.

Sylvestre, P., Couture-Tosi, E., and Mock, M. (2003) Polymorphism in the collagen-like region of the Bacillus anthracis BclA protein leads to variation in exosporium filament length. J. Bacterial. 185: 1555-1563.

Swiecki, M. K., Lisanby, M. W., Shu, F., Turnbough, C. L. Jr, and Kearney, J. P. (2006) Monoclonal antibodies for Bacillus anthracis spore detection and functional analyses of spore germination and outgrowth. J. Immunol. 176: 6076-6084.

Thompson, B. M., Walter, L. N., Fox, K. F., Fox, A., and Stewart, G. C. (2007) The BclB glycoprotein of Bacillus anthracis is involved in exosporium integrity. J. Bacterial. 189: 6704-6713.

Thompson B M and Stewart G C. (2008) Targeting of the BclA and BclB proteins to the Bacillus anthracis spore surface. Mol Microbial. 70: 421-434.

Turnbull, P. C. B. (1991) Anthrax vaccines: past, present and future. Vaccine 9: 533-539.

Waller, L. N., Stump, M. J., Fox, K. F., Harley, W. M., Fox, A., Stewart, G. C., and Shahgholi, M. (2005) Identification of a second collagen-like glycoprotein produced by Bacillus anthracis and demonstration of associated spore-specific sugars. J. Bacterial. 187: 4592-4597.

Weaver, J., Kang, T. J., Raines, K. W., Cao, G. L., Hibbs, S., Tsai, P., Baillie, L., Rosen, G. M., and Cross, A. S. (2007) Protective role of Bacillus anthracis exosporium in macrophagemediated killing by nitric oxide. Infect. Immun. 75:3894-3901.

Yang, F., Moss, L. G., and Phillips, G. N. Jr. (1996) The molecular structure of green fluorescent protein. Nature Biotech. 14: 1246-1251.

What is claimed is:

1. A *Bacillus* exosporium molecule delivery (BEMD) system comprising a recombinant *Bacillus cereus* family member expressing a fusion construct, wherein the fusion construct comprises at least one molecule of interest (MOI) and:
   (a) a targeting sequence comprising amino acids 1-28 of SEQ ID NO: 10;
   (b) a targeting sequence comprising amino acids 13-28 of SEQ ID NO: 10;
   (c) a targeting sequence comprising SEQ ID NO: 10; or
   (d) a targeting sequence having at least 50% identity with amino acids 13-28 of SEQ ID NO: 10, wherein the identity with amino acids 18-28 of SEQ ID NO: 10 is at least 63%;
   and wherein expression of the fusion construct results in display of the MOI on the exosporium of the recombinant *Bacillus cereus* family member.

2. The BEMD system of claim 1, wherein the recombinant *Bacillus cereus* family member is selected from the group consisting of strains of *B. anthracis, B. cereus, B. thuringiensis*, and combinations thereof.

3. The BEMD system of claim 1, wherein the MOI is an immunogenic molecule.

4. The BEMD system of claim 3, wherein the immunogenic molecule of the fusion construct is physically oriented in the exosporium to be able to stimulate an immune response.

5. A method of making a delivery system comprising:
   a) constructing a fusion construct, wherein the fusion construct comprises at least one MOI and:
      (i) a targeting sequence comprising amino acids 1-28 of SEQ ID NO: 10;
      (ii) a targeting sequence comprising amino acids 13-28 of SEQ ID NO: 10;
      (iii) a targeting sequence comprising SEQ ID NO: 10; or
      (iv) a targeting sequence having at least 50% identity with amino acids 13-28 of SEQ ID NO: 10, wherein the identity with amino acids 18-28 of SEQ ID NO: 10 is at least 63%;
   b) cloning the fusion construct into a shuttle plasmid; and
   c) electroporating the shuttle plasmid containing the fusion construct into a *Bacillus cereus* family member, wherein expression of the fusion construct results in display of the MOI on the exosporium of the *Bacillus cereus* family member.

6. The method of claim 5, wherein the *Bacillus cereus* family member is selected from the group consisting of strains of *B. anthracis, B. cereus, B. thuringiensis*, and combinations thereof.

7. The method of claim 5, wherein the MOI is an immunogenic molecule.

8. The method of claim 7, wherein the immunogenic molecule of the fusion construct is physically oriented in the exosporium to be able to stimulate an immune response.

9. A kit comprising the delivery system of claim 1.

10. The kit of claim 9, wherein the recombinant *Bacillus cereus* family member is selected from the group consisting of strains of *B. anthracis, B. cereus, B. thuringiensis*, and combinations thereof.

11. The kit of claim 9, wherein the MOI is an immunogenic molecule.

12. The kit of claim 11, wherein the immunogenic molecule of the fusion construct is physically oriented in the exosporium to be able to stimulate an immune response.

13. A method of using a delivery system comprising administering to a subject the recombinant a recombinant *Bacillus cereus* family member of claim 1.

14. The method of claim 13, wherein the recombinant *Bacillus cereus* family member is selected from the group consisting of strains of *B. anthracis, B. cereus, B. thuringiensis*, and combinations thereof.

15. The method of claim 13, wherein the MOI is an immunogenic molecule.

16. The method of claim 15, wherein the immunogenic molecule of the fusion construct is physically oriented in the exosporium to be able to stimulate an immune response.

17. The BEMD system of claim 2, wherein the recombinant *Bacillus cereus* family member comprises *B. thuringiensis*.

18. The method of claim 6, wherein the recombinant *Bacillus cereus* family member comprises *B. thuringiensis*.

19. The kit of claim 10, wherein the recombinant *Bacillus cereus* family member comprises *B. thuringiensis*.

20. The method of claim 14, wherein the recombinant *Bacillus cereus* family member comprises *B. thuringiensis*.

21. The BEMD system of claim 1, wherein the fusion construct is expressed under the control of a BclA promoter.

22. The BEMD system of claim 1, wherein the *Bacillus cereus* family member is inactivated.

23. The method of claim 13, further comprising inactivating the *Bacillus cereus* family member prior to administration.

* * * * *

SEQUENCE LISTING

<160> NUMBER OF SEQ ID NOS: 64

<210> SEQ ID NO 1
<211> LENGTH: 35
<212> TYPE: PRT
<213> ORGANISM: Bacillus spp

<400> SEQUENCE: 1

```
Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
```

```
                    20                  25                  30

Ile Pro Pro
        35

<210> SEQ ID NO 2
<211> LENGTH: 32
<212> TYPE: PRT
<213> ORGANISM: Bacillus spp

<400> SEQUENCE: 2

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
                20                  25                  30

<210> SEQ ID NO 3
<211> LENGTH: 31
<212> TYPE: PRT
<213> ORGANISM: Bacillus spp

<400> SEQUENCE: 3

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro Phe Thr Phe Pro
                20                  25                  30

<210> SEQ ID NO 4
<211> LENGTH: 36
<212> TYPE: PRT
<213> ORGANISM: Bacillus spp

<400> SEQUENCE: 4

Met Val Lys Val Val Glu Gly Asn Gly Gly Lys Ser Lys Ile Lys Ser
1               5                   10                  15

Pro Leu Asn Phe Lys Ile Leu Ser Asp Leu Val Gly Pro Thr Phe Pro
                20                  25                  30

Pro Val Pro Thr
        35

<210> SEQ ID NO 5
<211> LENGTH: 17
<212> TYPE: PRT
<213> ORGANISM: Bacillus spp

<400> SEQUENCE: 5

Met Ala Phe Asp Pro Asn Leu Val Gly Pro Thr Leu Pro Pro Ile Pro
1               5                   10                  15

Pro

<210> SEQ ID NO 6
<211> LENGTH: 27
<212> TYPE: PRT
<213> ORGANISM: Bacillus spp

<400> SEQUENCE: 6

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro
                20                  25

<210> SEQ ID NO 7
```

```
<211> LENGTH: 41
<212> TYPE: PRT
<213> ORGANISM: Bacillus spp

<400> SEQUENCE: 7

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro Phe Thr Leu Pro Thr Gly
        35                  40

<210> SEQ ID NO 8
<211> LENGTH: 33
<212> TYPE: PRT
<213> ORGANISM: Bacillus spp

<400> SEQUENCE: 8

Met Ser Glu Lys Tyr Ile Ile Leu His Gly Thr Ala Leu Glu Pro Asn
1               5                   10                  15

Leu Ile Gly Pro Thr Leu Pro Pro Ile Pro Pro Phe Thr Phe Pro Asn
            20                  25                  30

Gly

<210> SEQ ID NO 9
<211> LENGTH: 44
<212> TYPE: PRT
<213> ORGANISM: Bacillus spp

<400> SEQUENCE: 9

Met Val Lys Val Val Glu Gly Asn Gly Gly Lys Ser Lys Ile Lys Ser
1               5                   10                  15

Pro Leu Asn Ser Asn Phe Lys Ile Leu Ser Asp Leu Val Gly Pro Thr
            20                  25                  30

Phe Pro Pro Val Pro Thr Gly Met Thr Gly Ile Thr
        35                  40

<210> SEQ ID NO 10
<211> LENGTH: 34
<212> TYPE: PRT
<213> ORGANISM: Bacillus spp

<400> SEQUENCE: 10

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro Ile His Ile Pro
            20                  25                  30

Thr Gly

<210> SEQ ID NO 11
<211> LENGTH: 13
<212> TYPE: PRT
<213> ORGANISM: Bacillus spp

<400> SEQUENCE: 11

Leu Ile Val Gly Pro Thr Leu Phe Pro Pro Ile Pro Pro
1               5                   10

<210> SEQ ID NO 12
<211> LENGTH: 35
<212> TYPE: PRT
```

<213> ORGANISM: Bacillus spp

<400> SEQUENCE: 12

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro
        35

<210> SEQ ID NO 13
<211> LENGTH: 17
<212> TYPE: PRT
<213> ORGANISM: Bacillus spp

<400> SEQUENCE: 13

Met Ala Phe Asp Pro Asn Leu Val Gly Pro Thr Leu Pro Pro Ile Pro
1               5                   10                  15

Pro

<210> SEQ ID NO 14
<211> LENGTH: 35
<212> TYPE: PRT
<213> ORGANISM: Bacillus spp

<400> SEQUENCE: 14

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro
        35

<210> SEQ ID NO 15
<211> LENGTH: 35
<212> TYPE: PRT
<213> ORGANISM: Bacillus spp

<400> SEQUENCE: 15

Met Ser Asn Asn Asn Tyr Ser Asn Gly Leu Asn Pro Asp Glu Ser Leu
1               5                   10                  15

Ser Ala Ser Ala Phe Asp Pro Asn Leu Val Gly Pro Thr Leu Pro Pro
            20                  25                  30

Ile Pro Pro
        35

<210> SEQ ID NO 16
<211> LENGTH: 24
<212> TYPE: PRT
<213> ORGANISM: Bacillus spp

<400> SEQUENCE: 16

Met Ser Asn Asn Asn Tyr Ser Asn Gly Leu Asn Pro Asp Glu Ser Leu
1               5                   10                  15

Ser Ala Ser Ala Phe Asp Pro Asn
            20

<210> SEQ ID NO 17
<211> LENGTH: 12
<212> TYPE: PRT
<213> ORGANISM: Bacillus spp

<400> SEQUENCE: 17

Met Leu Val Gly Pro Thr Leu Pro Pro Ile Pro Pro
1               5                   10

<210> SEQ ID NO 18
<211> LENGTH: 1
<212> TYPE: PRT
<213> ORGANISM: Bacillus spp

<400> SEQUENCE: 18

Met
1

<210> SEQ ID NO 19
<211> LENGTH: 28
<212> TYPE: PRT
<213> ORGANISM: Bacillus spp

<400> SEQUENCE: 19

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro
            20                  25

<210> SEQ ID NO 20
<211> LENGTH: 28
<212> TYPE: PRT
<213> ORGANISM: Bacillus spp

<400> SEQUENCE: 20

Met Lys Gln Asn Asp Lys Leu Trp Leu Asp Lys Gly Ile Ile Gly Pro
1               5                   10                  15

Glu Asn Ile Gly Pro Thr Phe Pro Val Leu Pro Pro
            20                  25

<210> SEQ ID NO 21
<211> LENGTH: 26
<212> TYPE: DNA
<213> ORGANISM: Bacillus spp

<400> SEQUENCE: 21
ctcgagtaat caccctcttc caaatc                                       26

<210> SEQ ID NO 22
<211> LENGTH: 37
<212> TYPE: DNA
<213> ORGANISM: Bacillus spp

<400> SEQUENCE: 22
ttaccaccga taccaccaat ggtgagcaag ggcgagg                            37

<210> SEQ ID NO 23
<211> LENGTH: 26
<212> TYPE: DNA
<213> ORGANISM: Bacillus spp

<400> SEQUENCE: 23
ctcgagtaat caccctcttc caaatc                                       26

<210> SEQ ID NO 24
<211> LENGTH: 42
<212> TYPE: DNA

<213> ORGANISM: Bacillus spp

<400> SEQUENCE: 24
ccattattat tgaaaaagtt gctatggtga gcaagggcga gg        42

<210> SEQ ID NO 25
<211> LENGTH: 26
<212> TYPE: DNA
<213> ORGANISM: Bacillus spp

<400> SEQUENCE: 25
ctcgagtaat caccctcttc caaatc        26

<210> SEQ ID NO 26
<211> LENGTH: 34
<212> TYPE: DNA
<213> ORGANISM: Bacillus spp

<400> SEQUENCE: 26
ggaggtgaat ttatggcatt tgaccctaat cttg        34

<210> SEQ ID NO 27
<211> LENGTH: 26
<212> TYPE: DNA
<213> ORGANISM: Bacillus spp

<400> SEQUENCE: 27
ctcgagtaat caccctcttc caaatc        26

<210> SEQ ID NO 28
<211> LENGTH: 48
<212> TYPE: DNA
<213> ORGANISM: Bacillus spp

<400> SEQUENCE: 28
aaggctgccg cagcgatgtc aaataataat tattcaaatg accatgat        48

<210> SEQ ID NO 29
<211> LENGTH: 26
<212> TYPE: DNA
<213> ORGANISM: Bacillus spp

<400> SEQUENCE: 29
ctcgagtaat caccctcttc caaatc        26

<210> SEQ ID NO 30
<211> LENGTH: 41
<212> TYPE: DNA
<213> ORGANISM: Bacillus spp

<400> SEQUENCE: 30
ccaccgatac caccaatgag taaaggagaa gaactttca c        41

<210> SEQ ID NO 31
<211> LENGTH: 26
<212> TYPE: DNA
<213> ORGANISM: Bacillus spp

<400> SEQUENCE: 31
ctcgagtaat caccctcttc caaatc        26

<210> SEQ ID NO 32
<211> LENGTH: 42

```
<212> TYPE: DNA
<213> ORGANISM: Bacillus spp

<400> SEQUENCE: 32
ttaccaccga taccaccaat gaccatgatt acgccaagct tg                    42

<210> SEQ ID NO 33
<211> LENGTH: 26
<212> TYPE: DNA
<213> ORGANISM: Bacillus spp

<400> SEQUENCE: 33
ctcgagtaat caccctcttc caaatc                                      26

<210> SEQ ID NO 34
<211> LENGTH: 42
<212> TYPE: DNA
<213> ORGANISM: Bacillus spp

<400> SEQUENCE: 34
acgctttatg gaggtgaatt tatgaccatg attacgccaa gc                    42

<210> SEQ ID NO 35
<211> LENGTH: 26
<212> TYPE: DNA
<213> ORGANISM: Bacillus spp

<400> SEQUENCE: 35
ctcgagtaat caccctcttc caaatc                                      26

<210> SEQ ID NO 36
<211> LENGTH: 79
<212> TYPE: DNA
<213> ORGANISM: Bacillus spp

<400> SEQUENCE: 36
tcaaatggat taaccccga tgaatcttta tcagctagtg catttgaccc taatatgacc  60
atgattacgc caagcttgc                                              79

<210> SEQ ID NO 37
<211> LENGTH: 26
<212> TYPE: DNA
<213> ORGANISM: Bacillus spp

<400> SEQUENCE: 37
ctcgagtaat caccctcttc caaatc                                      26

<210> SEQ ID NO 38
<211> LENGTH: 58
<212> TYPE: DNA
<213> ORGANISM: Bacillus spp

<400> SEQUENCE: 38
atgcttgtag gacctacatt accaccgata ccaatgacca tgattacgcc aagcttgc   58

<210> SEQ ID NO 39
<211> LENGTH: 27
<212> TYPE: DNA
<213> ORGANISM: Bacillus spp

<400> SEQUENCE: 39
ctcgagatta gaacgtaacc aatttag                                     27
```

<210> SEQ ID NO 40
<211> LENGTH: 45
<212> TYPE: DNA
<213> ORGANISM: Bacillus spp

<400> SEQUENCE: 40
accttcccgg ttcttccccc aatgaccatg attacgccaa gcttg                45

<210> SEQ ID NO 41
<211> LENGTH: 26
<212> TYPE: DNA
<213> ORGANISM: Bacillus spp

<400> SEQUENCE: 41
ctcgagtaat caccctcttc caaatc                                     26

<210> SEQ ID NO 42
<211> LENGTH: 45
<212> TYPE: DNA
<213> ORGANISM: Bacillus spp

<400> SEQUENCE: 42
acgctttatg gaggtgaatt tatgaaacag aatgacaaat tatgg                45

<210> SEQ ID NO 43
<211> LENGTH: 37
<212> TYPE: DNA
<213> ORGANISM: Bacillus spp

<400> SEQUENCE: 43
cctcgccctt gctcaccatt ggtggtatcg gtggtaa                         37

<210> SEQ ID NO 44
<211> LENGTH: 31
<212> TYPE: DNA
<213> ORGANISM: Bacillus spp

<400> SEQUENCE: 44
gcctcgagtt acttgtacag ctcgtccatg c                               31

<210> SEQ ID NO 45
<211> LENGTH: 42
<212> TYPE: DNA
<213> ORGANISM: Bacillus spp

<400> SEQUENCE: 45
cctcgccctt gctcaccata gcaacttttt caataataat gg                   42

<210> SEQ ID NO 46
<211> LENGTH: 31
<212> TYPE: DNA
<213> ORGANISM: Bacillus spp

<400> SEQUENCE: 46
gcctcgagtt acttgtacag ctcgtccatg c                               31

<210> SEQ ID NO 47
<211> LENGTH: 34
<212> TYPE: DNA
<213> ORGANISM: Bacillus spp

<400> SEQUENCE: 47
gattagggtc aaatgccata aattcacctc cata                            34

<210> SEQ ID NO 48
<211> LENGTH: 31
<212> TYPE: DNA
<213> ORGANISM: Bacillus spp

<400> SEQUENCE: 48
gcctcgagtt acttgtacag ctcgtccatg c                          31

<210> SEQ ID NO 49
<211> LENGTH: 36
<212> TYPE: DNA
<213> ORGANISM: Bacillus spp

<400> SEQUENCE: 49
catcgctgcg gcagccttgt acagctcgtc catgcc                     36

<210> SEQ ID NO 50
<211> LENGTH: 30
<212> TYPE: DNA
<213> ORGANISM: Bacillus spp

<400> SEQUENCE: 50
ctcgagttat tgtagagct catccatgcc                             30

<210> SEQ ID NO 51
<211> LENGTH: 42
<212> TYPE: DNA
<213> ORGANISM: Bacillus spp

<400> SEQUENCE: 51 ttctcctttta ctcattggtg gtatcggtgg taatgtaggt cc             42

<210> SEQ ID NO 52
<211> LENGTH: 30
<212> TYPE: DNA
<213> ORGANISM: Bacillus spp

<400> SEQUENCE: 52
ctcgagttat tgtagagct catccatgcc                             30

<210> SEQ ID NO 53
<211> LENGTH: 42
<212> TYPE: DNA
<213> ORGANISM: Bacillus spp

<400> SEQUENCE: 53
tggcgtaatc atggtcattg gtggtatcgg tggtaatgta gg              42

<210> SEQ ID NO 54
<211> LENGTH: 33
<212> TYPE: DNA
<213> ORGANISM: Bacillus spp

<400> SEQUENCE: 54
ctcgagtaaa ggaacagatg gtggcgtccc tcg                        33

<210> SEQ ID NO 55
<211> LENGTH: 47
<212> TYPE: DNA
<213> ORGANISM: Bacillus spp

<400> SEQUENCE: 55
caagcttggc gtaatcatgg tcataaattc acctccataa agcgttc        47

<210> SEQ ID NO 56
<211> LENGTH: 33
<212> TYPE: DNA
<213> ORGANISM: Bacillus spp

<400> SEQUENCE: 56
ctcgagtaaa ggaacagatg gtggcgtccc tcg        33

<210> SEQ ID NO 57
<211> LENGTH: 73
<212> TYPE: DNA
<213> ORGANISM: Bacillus spp

<400> SEQUENCE: 57
gctgataaag attcatcggg gtttaatcca tttgaataat tattatttga cataaattca        60
cctccataaa gcg        73

<210> SEQ ID NO 58
<211> LENGTH: 33
<212> TYPE: DNA
<213> ORGANISM: Bacillus spp

<400> SEQUENCE: 58
ctcgagtaaa ggaacagatg gtggcgtccc tcg        33

<210> SEQ ID NO 59
<211> LENGTH: 53
<212> TYPE: DNA
<213> ORGANISM: Bacillus spp

<400> SEQUENCE: 59
tggtatcggt ggtaatgtag gtcctacaag cataaattca cctccataaa gcg        53

<210> SEQ ID NO 60
<211> LENGTH: 33
<212> TYPE: DNA
<213> ORGANISM: Bacillus spp

<400> SEQUENCE: 60
ctcgagtaaa ggaacagatg gtggcgtccc tcg        33

<210> SEQ ID NO 61
<211> LENGTH: 38
<212> TYPE: DNA
<213> ORGANISM: Bacillus spp

<400> SEQUENCE: 61
tggcgtaatc atggtcattg ggggaagaac cgggaagg        38

<210> SEQ ID NO 62
<211> LENGTH: 33
<212> TYPE: DNA
<213> ORGANISM: Bacillus spp

<400> SEQUENCE: 62
ctcgagtaaa ggaacagatg gtggcgtccc tcg        33

<210> SEQ ID NO 63
<211> LENGTH: 44
<212> TYPE: DNA
<213> ORGANISM: Bacillus spp

```
<400> SEQUENCE: 63
cataatttgt cattctgttt cataaattca cctccataaa gcgt            44

<210> SEQ ID NO 64
<211> LENGTH: 33
<212> TYPE: DNA
<213> ORGANISM: Bacillus spp

<400> SEQUENCE: 64
ctcgagtaaa ggaacagatg gtggcgtccc tcg                        33
```